(12) United States Patent
Robey

(10) Patent No.: US 9,724,484 B2
(45) Date of Patent: Aug. 8, 2017

(54) BREATHING APPARATUS AND METHOD OF USE

(75) Inventor: Eric J Robey, Colliers, WV (US)

(73) Assignee: Draeger Medical Systems, Inc., Andover, MA (US)

( * ) Notice: Subject to any disclaimer, the term of this patent is extended or adjusted under 35 U.S.C. 154(b) by 391 days.

(21) Appl. No.: 14/370,501

(22) PCT Filed: Jan. 5, 2012

(86) PCT No.: PCT/US2012/020258
§ 371 (c)(1),
(2), (4) Date: Jul. 3, 2014

(87) PCT Pub. No.: WO2013/103343
PCT Pub. Date: Jul. 11, 2013

(65) Prior Publication Data
US 2015/0047638 A1   Feb. 19, 2015

(51) Int. Cl.
*A61M 16/00* (2006.01)
*A61B 7/02* (2006.01)
(Continued)

(52) U.S. Cl.
CPC .... *A61M 16/0003* (2014.02); *A61M 16/0087* (2013.01); *A61M 16/0616* (2014.02);
(Continued)

(58) Field of Classification Search
CPC .......... A61M 16/0003; A61M 16/0616; A61M 16/20; A61M 16/201; A61M 16/202;
(Continued)

(56) References Cited

U.S. PATENT DOCUMENTS

| 5,127,398 A * | 7/1992 | Stone | A62B 9/02 128/204.18 |
| 2006/0191533 A1* | 8/2006 | Brookman | A62B 7/02 128/201.25 |

(Continued)

FOREIGN PATENT DOCUMENTS

| DE | 195 03 027 | 3/1996 |
| WO | WO/2004/093997 | 11/2004 |

(Continued)

*Primary Examiner* — Lynne Anderson
*Assistant Examiner* — Elliot S Ruddie
(74) *Attorney, Agent, or Firm* — Jones Day

(57) ABSTRACT

A breathing apparatus includes a source of compressed air and a lung demand valve that receives compressed air from the source. A pneumatic valve assembly is connected between the source and the lung demand valve. The pneumatic valve assembly is moveable between a first closed position that prevents a flow of compressed air to the lung demand valve and a second open position that provides a path for compressed air to flow to the lung demand valve. A mask receives the lung demand valve therein. The mask provides the compressed air to a user and having a first operational mode providing filtered ambient air to the user and a second operational mode providing compressed air to the user. A control device is coupled to the pneumatic valve assembly. The control device detects a condition in the air surrounding the apparatus and controlling the pneumatic valve assembly to move between the first closed and second open position and the mask to operate in a respective one of the first and second operational modes.

21 Claims, 20 Drawing Sheets

(51) Int. Cl.
| | |
|---|---|
| *A61B 18/08* | (2006.01) |
| *A61M 16/06* | (2006.01) |
| *A61M 16/20* | (2006.01) |
| *A61M 16/08* | (2006.01) |
| *A62B 7/02* | (2006.01) |
| *A62B 7/10* | (2006.01) |
| *A62B 9/02* | (2006.01) |
| *A62B 9/04* | (2006.01) |
| *A62B 18/08* | (2006.01) |

(52) U.S. Cl.
CPC ...... *A61M 16/0875* (2013.01); *A61M 16/205* (2014.02); *A62B 7/02* (2013.01); *A62B 7/10* (2013.01); *A62B 9/02* (2013.01); *A62B 9/04* (2013.01); *A62B 18/08* (2013.01); *A61M 2016/0027* (2013.01); *A61M 2205/3331* (2013.01)

(58) Field of Classification Search
CPC .............. A61M 16/203; A61M 16/204; A61M 16/205; A61M 16/206; A61M 16/207; A61M 16/208; A61M 16/209; A61M 16/22; A61M 16/0087; A61M 16/009; A61M 16/0093; A61M 16/0875; A61M 2016/00; A61M 16/0051; A61M 2205/33; A61M 2205/50; A61M 2205/58; A61B 5/742; A61B 5/746; A61B 5/4839; A61B 5/14551; A62B 7/00; A62B 7/02; A62B 7/04; A62B 7/06; A62B 7/10; A62B 9/006; A62B 9/02; A62B 9/022; A62B 9/04; A62B 9/06; A62B 18/00; A62B 18/04; A62B 18/045; A62B 18/08

USPC ........... 128/201.22, 201.23, 201.24, 201.25, 128/201.26, 201.27, 201.28, 201.29, 128/202.11, 204.29, 204.22, 204.21, 128/204.18, 204.26, 200.24, 202.22, 128/205.23

See application file for complete search history.

(56) References Cited

U.S. PATENT DOCUMENTS

| | | | |
|---|---|---|---|
| 2007/0235030 A1* | 10/2007 | Teetzel | A62B 7/10 128/205.12 |
| 2010/0078025 A1* | 4/2010 | Grilliot | A62B 9/006 128/204.21 |
| 2011/0041848 A1* | 2/2011 | Stone | A61M 16/12 128/203.14 |

FOREIGN PATENT DOCUMENTS

| | | |
|---|---|---|
| WO | WO/2006/012475 | 2/2006 |
| WO | WO/2010/091002 | 8/2010 |

* cited by examiner

BREATHING APPARATUS AND METHOD OF USE

CROSS-REFERENCE TO RELATED APPLICATIONS

This application is a National Stage Application, filed under 35 U.S.C. §371, of International Application No. PCT/US2012/020258, filed on Jan. 5, 2012, the contents of which are hereby fully incorporated by reference in its entirety.

FIELD OF THE INVENTION

This invention concerns a system and method of using a breathing apparatus, and more specifically, to automatically modify a breathing mode of a breathing apparatus in response to environmental conditions.

BACKGROUND OF THE INVENTION

There are many environments where air quality is insufficient for respiration due to insufficient oxygen concentration and/or contamination by unsafe particulate or gaseous matter. Yet, in these environments, it is important to be able to function normally in order to perform certain tasks. An example of this type of environment is a smoke-filled building which must be navigated by firefighters in order to render buildings safe as well as to rescue persons who may be trapped in this environment. Another example of a contaminate-rich environment may include a structure that has been overcome by a gas which may be harmful. This may occur, for example, during a military operation where adversaries release a toxic or otherwise unsafe gas to prevent capture.

There have been many advances in breathing apparatuses that have assisted functioning and respiration in these environments while tasks are performed. One example is a self contained breathing apparatus (SCBA) which is a wearable apparatus that includes a cylinder of compressed air, pressure reducer, lung demand valve (LDV) and a mask capable of maintaining a positive pressure therein. A SCBA apparatus provides a high degree of protection in view of its dedicated supply of compressed air in conjunction with the mask maintaining a positive pressure thereby forcing any contaminates that may enter the mask via a leak or incomplete seal out of the mask. A drawback associated with the SCBA apparatus is the storage capacity of the cylinder retaining compressed air. These cylinders have a finite capacity and, in environments of high stress, respiration increases thereby depleting the compressed air at a higher rate and potentially placing the user in danger of lacking breathable oxygen.

Another example of breathing apparatuses are negative pressure respirators which have masks that include at least one type of filter but which maintain the mask in a negative pressure state. These masks typically include air purifying respirators (APR) or powered air purifying respirators (PAPR) that selectively filter contaminates from the air as the person wearing the mask inhales. In operation, the user creates a vacuum inside the mask, by inhaling, to draw in air from the outside, through the filter. While different filters can protect against different contaminates in the air, these filters cannot protect a user from oxygen deficiency in the air. Only a SCBA apparatus with its own dedicated supply of air can protect a user against oxygen deficient air. In the case where the negative respirator includes a PAPR, the battery powered PAPR draws air through the filters and provides the power-filtered air through a breathing hose and into the user's mask. However, as the mask remains in a negative pressure state, any air flowing into the mask and not inhaled by the user will flow freely out from an exhalation valve in the mask.

Another device attempts to combine the SCBA apparatus, a PAPR device and a mask that may operate in one of a negative pressure mode or a positive pressure mode. This allows the user to breathe in filtered contaminate-free air and also provide the added protection of having a dedicated supply of clean compressed air in case the user finds themselves in a suddenly oxygen deficient environment. However, a drawback associated with this type of apparatus is the apparatus must be manually switched from a negative pressure state to a positive pressure state. Since a user needing to make the switch is likely in a compromising and difficult setting, any time delay associated with switching sources of air to a mask could have severe consequences for the user wearing the apparatus as well as those the user is charged with protecting.

Thus, a need exists to provide a breathing apparatus that automatically switches a mask from negative pressure to positive pressure to enable the user to breathe from a dedicated supply of compressed air without any delay. An apparatus according to invention principles addresses deficiencies of known pressure control apparatus.

SUMMARY OF THE INVENTION

In one embodiment, a breathing apparatus includes a source of compressed air and a lung demand valve that receives compressed air from the source. A pneumatic valve assembly is connected between the source and the lung demand valve. The pneumatic valve assembly is moveable between a first closed position that prevents a flow of compressed air to the lung demand valve and a second open position that provides a path for compressed air to flow to the lung demand valve. A mask receives the lung demand valve therein. The mask provides the compressed air to a user and having a first operational mode providing filtered ambient air to the user and a second operational mode providing compressed air to the user. A control device is coupled to the pneumatic valve assembly. The control device detects a condition in the air surrounding the apparatus and controlling the pneumatic valve assembly to move between the first closed and second open position and the mask to operate in a respective one of the first and second operational modes.

In another embodiment, a method of using a breathing apparatus comprises the activities of providing compressed air from a source of compressed air and receiving compressed air from the source at a lung demand valve. Compressed air is received from the lung demand valve at a mask. The mask has a first operational mode providing filtered ambient air to the user and a second operational mode providing compressed air to the user. A condition in air surrounding the apparatus is detected and a pneumatic valve assembly connected between the source and the lung demand valve is controlled using a control device to move between a first closed that prevents a flow of compressed air to the lung demand valve and a second open position that provides a path through with the compressed air may flow. The mask is operated in a first operational mode in response to the pneumatic valve assembly being in the first closed position preventing compressed air from flowing through the pneumatic valve assembly and a second operational mode in response to the pneumatic valve assembly being in the second open position providing a passage for compressed air to flow through the pneumatic valve assembly.

In a further embodiment, a pneumatic valve assembly that selectively couples a source of compressed air with a lung demand valve is provided. The pneumatic valve assembly includes an inlet coupled to the source for receiving compressed air. A first pressure reducer is coupled to receive compressed air from the inlet. The first pressure reducer reduces a pressure of the compressed air to generate a first pneumatic signal. The assembly also includes a pneumatic valve. The pneumatic valve includes a first input, a second input coupled to the inlet to receive compressed air and an outlet coupled to the lung demand valve. A piston in the pneumatic valve is moveable between a first position preventing the compressed air from flowing from the inlet to the outlet and a second position enabling the compressed air to flow from the inlet to the outlet. A solenoid valve is coupled between the first pressure reducer and the first input of the pneumatic valve, the solenoid moveable between a first closed position preventing passage of the first pneumatic signal from the first pressure reducer to the pneumatic valve and a second open position enabling passage of the first pneumatic signal from the first pressure reducer to the pneumatic valve, wherein compressed air is prevented from flowing from said second input to the outlet of the pneumatic valve assembly when said solenoid is in the first closed position and compressed air is permitted to flow from said second input to the outlet of the pneumatic valve assembly when the solenoid is in the second open position.

In another embodiment, a method of operating a pneumatic valve assembly to provide compressed air from a source of compressed air to a lung demand valve is provided. Pressure of compressed air received through an inlet of the pneumatic valve assembly is reduced using a first pressure reducer to generate a first pneumatic signal. The first pneumatic signal is selectively provided to a pneumatic valve and the pneumatic valve is moveable between a first a first position preventing the compressed air from flowing through the pneumatic valve assembly and a second position enabling the compressed air to flow through the pneumatic valve assembly to the lung demand valve.

In a further embodiment, a lung demand valve that selectively controls an operational mode of a mask connected thereto is provided. The lung demand valve includes a housing and a connector extending from a surface of the housing enabling connection with the mask. The connector includes a first notch and a second notch extending around a perimeter of an exterior surface of the connector and separated by a gap. An output port extends through the connector and positioned within the gap.

In yet another embodiment, a method of using a lung demand valve for selectively controlling an operational mode of a mask connected thereto is provided. Compressed air is received at an input port of the lung demand valve and a second pneumatic signal is generated by an operational mode switch using the compressed air received at the input port of the lung demand valve. The second pneumatic signal is provided to an output port on a connector of the lung demand valve used to connect a mask to the lung demand valve.

A further embodiment includes a mask for use with a breathing apparatus. The mask includes a faceplate having a window enabling a user wearing the mask to see out thereof and a connection section enabling connection of the mask to a lung demand valve. The connection section includes an exhalation valve that enables air to flow out from within the mask and a bridge assembly for selectively closing the exhalation valve. A spring connects the bridge assembly to the exhalation valve, the spring moveable between an uncompressed position allowing air to flow through the exhalation valve and a compressed position preventing air from flowing through the exhalation valve. An actuator is connected to the bridge assembly, wherein in response to receiving a pneumatic control signal from the lung demand valve, the actuator and the bridge assembly cause the spring to move between the uncompressed and compressed positions.

Another embodiment including a method of configuring a mask for use with a breathing apparatus between a first negative pressure mode and a second positive pressure mode is provided. A pneumatic signal is received from a lung demand valve coupled to the mask. An actuator connected to a bridge assembly is actuated upon receiving the pneumatic signal from the lung demand valve. A spring that is coupled between the bridge assembly and an exhalation valve is compressed and the exhalation valve is covered thereby preventing air flowing through the exhalation valve and switching from the first negative pressure mode to the second positive pressure mode.

DETAILED DESCRIPTION

Figure 1:
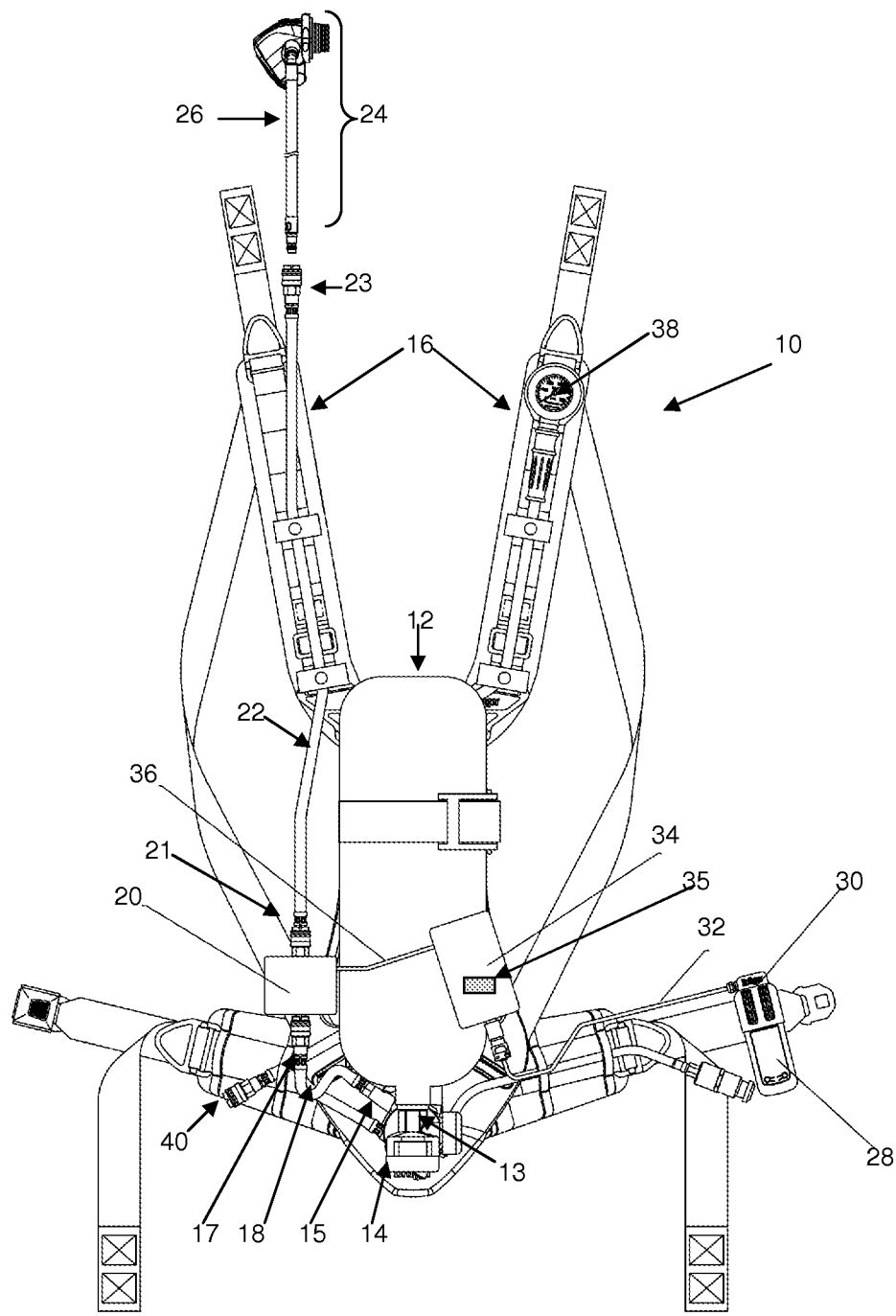
FIG. 1 is an illustrative view of a breathing apparatus according to invention principles.

The breathing apparatus according to invention principles advantageously enables a user to operate a breathing mask in a negative pressure mode allowing intake of filtered ambient air and automatically and immediately switching the mask to operate in a positive pressure mode in response to detecting at least one environmental characteristic indicating that a dedicated source of compressed air is needed. The breathing apparatus advantageously includes at least one sensor for sensing at least one environmental characteristic of the ambient environment. The at least one sensor may sense a plurality of different environmental characteristics that may require a change in the type of breathing mode employed by the apparatus at a given time.

In a first mode of operation, the mask associated with the breathing apparatus is in negative pressure mode such that the user may intake filtered ambient air. In this first negative pressure mode, an exhalation valve in the mask is selectively covered via an exhalation valve spring and a minimal force may partially compress the spring, displace the cover and allow air to flow out of the exhalation valve. In a second mode of operation, the mask associated with the breathing apparatus operates in a positive pressure mode whereby the exhalation valve spring is automatically compressed increasing a resistance required to displace the exhalation valve reducing an amount of air able to flow out therefrom. In this second mode of operation, air from a dedicated source of compressed air is provided to the mask via the breathing hose or the lung demand valve. In both the first and second mode of operation, the dedicated source of compressed air is advantageously engaged such that air can flow freely from the source for immediate use.

The breathing apparatus further advantageously includes a selectively controllable pneumatic valve assembly (e.g. a pilot valve) connected between the source of compressed air and the mask. As used hereinafter, the terms pilot valve assembly and pneumatic valve assembly may be used interchangeably. Additionally, the terms pilot valve and pneumatic valve may also be used interchangeably throughout the description of the breathing apparatus according to invention principles. The pilot valve prevents the compressed air from flowing into the mask when in the first negative pressure mode of operation. The pilot valve is advantageously controlled by a control processor that receives a sensor signal from the at least one sensor and determines that an alarm condition associated with the ambient air has been reached. The pilot valve is automatically controlled to create and use a first pneumatic signal to open the valve and let compressed air from the source of compressed air flow into a lung demand valve which provides the compressed air to the mask in a known manner. When compressed air reaches a lung demand valve, an operational mode switch assembly is controlled via a second pneumatic signal to automatically compress the exhalation valve spring in the mask to switch from the first mode of operation to the second mode of operation.

The apparatus further advantageously includes an indicator positioned at the mask and electrically coupled to the control processor which may selectively notify the user about at least one operational characteristic thereby providing the user with information about at least one of (a) environmental characteristics of the ambient air; (b) operation mode of the breathing apparatus; and (c) at least one characteristic with the source of compressed air. This advantageously provides an increased amount of information to the user which may be used while performing their task.

An exemplary embodiment of the breathing apparatus 10 is depicted in FIG. 1. The breathing apparatus 10 includes a source of compressed air 12 including a selectively controllable dispensing valve 14 from which the compressed air in the source 12 is dispensed. The dispensing valve 14 may be moveable from a first open position enabling compressed air to flow freely therethrough and a second closed position that prevents air flow from the source of compressed air 12. A pressure reducer 13 is coupled to the dispensing valve 14. The pressure reducer 13 reduces a pressure of the compressed air from a tank pressure (e.g. ~4500 psi) to a medium pressure (e.g. ~120 psi). This reduced medium pressure is the pressure at which the compressed air may be used by the various components of the apparatus 10 described below. Thus, hereinafter, compressed air from the source 12 will refer to compressed air that has been reduced by the pressure reducer 13.

A first connection tube 18 is releasably connected to the pressure reducer 13 mounted on the dispensing valve 14 of the source of compressed air 12 at a first end 15 thereof. A second end 17 of the first connection tube 18 is releasably connected to an input port of a pilot valve assembly 20. The pilot valve assembly 20 is selectively controllable to move between a first closed position preventing any air from flowing therethrough and a second open position enabling air flow through the pilot valve assembly 20. The operation of the pilot valve assembly 20 will be described in greater detail with respect to FIGS. 6-8. An output port of the pilot valve assembly 20 may be releasably connected to a first end 21 of a second connection tube 22. A second end 23 of the second connection tube 22 is connected to a breathing hose 26 of a lung demand valve (LDV) 24. The LDV 24 is releasably connected to a mask wearable by a user. An exemplary mask will be discussed hereinafter with respect to FIGS. 9-11. The LDV further includes an operational mode switch that selectively receives a pneumatic control signal and provides the pneumatic control signal to the mask to change the operational mode of the mask from a first negative pressure mode to a second positive pressure mode. The operational switch will be discussed in greater detail with respect to FIGS. 10 and 11.

When the pilot valve assembly 20 is in the first closed position, compressed air from the source 12 flows into the first connection tube 18 via the dispensing valve 14 but is prevented from flowing through the pilot valve assembly 20. This enables the breathing apparatus 10 to operate in negative pressure mode (e.g. first operational mode) whereby the user is able to breathe filtered ambient air. When the pilot valve assembly 20 is in the second open position, compressed air from the source 12 flows through the dispensing valve 14, the pressure reducer 13, first connection tube 18, pilot valve assembly 20 and second connection tube 22. From the second connection tube 22, the compressed air flows into the breathing hose 26 of the LDV 24 which provides breathable, uncontaminated air to the mask described below in FIG. 12-16. Additionally, the compressed air provided to the LDV is siphoned off for use by the operational mode switch as the pneumatic pressure signal which is provided to the mask and selectively causes the mask to change operational modes from the first negative pressure mode to the second positive pressure mode. The use of the pneumatic signal generated by the operational switch of the LDV advantageously automatically enables the breathing apparatus 10 to operate in the positive pressure mode (e.g. second operational mode).

The breathing apparatus 10 further includes a sensor 28 that selectively senses the presence and amounts of at least one characteristic associated with the ambient air. The term sensor 28 is being used for purposes of example only and any device able to sense environmental characteristics may be used. Additionally, persons skilled in the art will appreciate that the sensor 28 may include a single sensor able to sense multiple environmental characteristics or a plurality of individual sensors able to sense individual environmental characteristics or any combination thereof. The at least one characteristic sensed by sensor 28 may include at least one of the presence and/or amounts of at least one of (a) oxygen; (b) carbon dioxide; (c) carbon monoxide; (d) hydrogen sulfide; (e) nitrogen dioxide; (f) sulfur dioxide; (g) phosphine; (h) hydrogen cyanide; (i) ammonia; (j) Chlorine; (k) Hydrogen; (l) ozone; (m) nitrous oxide; (n) amines; (o) mercaptans; (p) phosgene; and (q) any combustible gaseous or particulate matter. In another embodiment, the at least one characteristic may include a contaminant present in the ambient air. A contaminant may be any particulate matter, gas or other substance present in the ambient air which may negatively affect the respiration of a user or cause the user discomfort, harm or illness. The sensor 28 may sense the ambient air to determine if a particular characteristic is present in the ambient air by determining the concentration (e.g., parts per million (ppm)) of the particular characteristic in the ambient air. The sensor 28 advantageously further includes configurable alarm levels associated with the respective characteristics sensed thereby. This advantageously allows a user, prior to using the breathing apparatus 10 including the sensor 28 to selectively configure the sensor 28 for use in a particular environment. For example, if the user is a firefighter the user may selectively configure the sensor to notify the user when an amount of carbon monoxide is determined to be at a particular level. This may indicate to the user that filtering of ambient air performed during negative pressure mode would be insufficient and notify the user that a dedicated source of compressed air from the source 12 is needed. The description of use during a situation including elevated levels of carbon dioxide is described for purposes of example only and one skilled in the art will appreciate that the sensor 28 may sense any environmental characteristic and notify the user that the sensed environment condition has reached a threshold level indicating an alarm condition.

The environmental characteristics sensed by the sensor 28 are advantageously used to control the operational mode of the breathing apparatus 10. The sensor 28 is removably coupled to an adapter 30 which is further coupled to an electronics housing 34 including a control processor 35 via an electrical connection 32. The sensor 28 includes a wireless communication transmitter and the adapter 30 includes a wireless communication receiver positioned therein. In one embodiment, the wireless communications transmitter is an infra-red (IR) transmitter and the receiver is an IR receiver. In another embodiment, the sensor 28 includes at least one electrical contact and the adapter 30 includes a matching electrical contact that enables data sensed by the sensor 28 to be provided to the control processor in the electronics housing. The sensor 28 and adapter 30 will be further described below in FIGS. 3-5. The adapter 30 advantageously enables users to use the breathing apparatus 10 with a plurality of different type of sensor devices 28 that presently exist. The lack of a direct wired connection between the sensor 28 and the control processor 35 makes the breathing apparatus 10 very versatile by allowing the user to advantageously plug and play different types of sensor devices 28 into the adapter 30 and allow the breathing apparatus 10 to effectively sense different environmental characteristics in different of environments.

The control processor 35 in the electronics housing 34 is further electrically connected to the pilot valve assembly 20 for controlling the operation of the pilot valve assembly 20 via a second electrical connection 36. In response to the sensor 28 sensing at least one environmental characteristic and the control processor 35 determining that the sensed at least one environmental characteristic has reached a threshold level, the control processor 35 generates a control signal which is provide to the pilot valve assembly 20 via the second electrical connection. The control signal causes the pilot valve assembly 20 to generate a pneumatic signal that is used in moving the pilot valve assembly 20 from the first closed position into the second open position allowing compressed air from the source 12 to flow therethrough.

Thus, the first mode of operation is the negative pressure mode enabling the user to breathe filtered ambient air using the mask. In the first mode of operation, the pilot valve assembly 20 is in the first closed position. In response to the sensor 28 sensing at least one environment characteristic and a determination by the control processor that the sensed characteristic has reached a threshold level, the control processor generates a control signal. The control signal is provided to the pilot valve assembly 20 enabling generation of a first pneumatic control signal causing the pilot valve assembly 20 to move from the first closed position to the second open position. The compressed air from the source flowing through the pilot valve assembly 20 is used by the operational switch in the LDV 24 to generate a second pneumatic signal which is provided to the mask and switches the operational mode of the mask from the first negative pressure mode to the second positive pressure mode in a manner discussed below.

Additionally, although not shown specifically herein, the electronics housing 34 includes a wireless transmitter that wirelessly communicates with an indicator positioned in the mask. The wireless transmitter may selectively communicate data representing at least one of the (a) sensed environmental characteristic; (b) a current operational mode of the apparatus; and (c) information associated with the source of compressed air 12. This data may be selectively displayed to a user via the indicator to provide additional information to the user. In one embodiment, the indicator may be a light emitting diode (LED) able to selectively be illuminated in different colors, wherein a particular color is associated with a particular type of data being communicated. In another embodiment, the indicator may include a plurality of different LEDs having different colors thereby enabling the user to be made aware of multiple different types of information at the same time.

Also shown in FIG. 1 is the breathing apparatus 10 being mounted on a harness 16. The harness 16 shown herein includes over-the-shoulder straps and a waist belt to secure the breathing apparatus 10 to a user. This is described for purpose of example only and the breathing apparatus may be mounted on any harness able to support the breathing apparatus 10 on the user. This may include, for example, a flexible harness or a rigid harness that may be removably positioned on a user to allow the user to perform a predetermined task while wearing the breathing apparatus 10. Additionally, the breathing apparatus 10 may also include other commonly known features of a SCBA system including a buddy breather 40 enabling the user to provide compressed air from the source to another person and a pressure gauge 38 connected to the source 12 providing the user with an indication as to an amount of pressure remaining in the source 12. While these additional features are useful during use of the breathing apparatus, they are not germane to the present invention and will not be discussed further.

Figure 2:
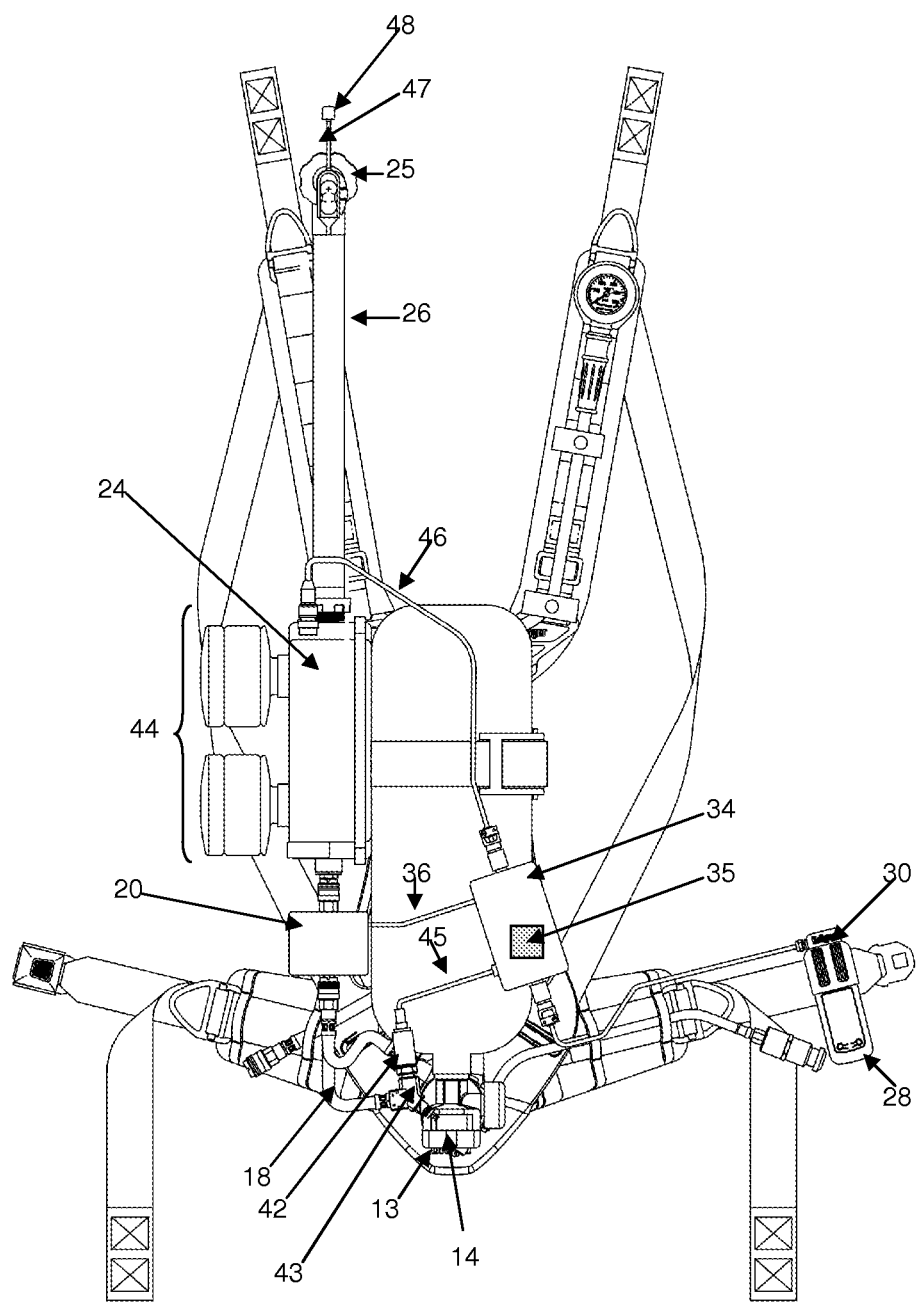
FIG. 2 is an illustrative view of an alternate embodiment of the breathing apparatus according to invention principles.

FIG. 2 depicts an alternate embodiment of the breathing apparatus 10'. The breathing apparatus 10' shown herein includes many similar elements that are connected and operate in a similar manner as described with respect to the breathing apparatus 10 in FIG. 1. Thus, these elements will not be further described in FIG. 2. The breathing apparatus includes a filtering device 44 coupled to the LDV 24. The LDV 24 is positioned between the output port of the pilot valve assembly 20 and the breathing hose 26. The LDV 24 receives filtered air from the filtering device 44 and provides the filtered ambient air through the breathing hose 26. The breathing hose 26 is selectively coupled to a mask such as the one described hereinbelow with respect to FIGS. 12-16 via a connector 25. In one embodiment, the filtering device 44 is a PAPR that selectively draws in and filters ambient air which is then provided to the LDV 24. In another embodiment, the filtering device 44 is a passive filter that draws and filters ambient air in response to inhalation by the user wearing the mask. The filtering device 44 may be able to filter any particular matter from the ambient air to provide the user with breathable air so long as the ambient air contains a sufficient amount of oxygen therein. In another embodiment, the filtering device 44 is electrically connected to the control processor 35 in the electronics housing 34 via a third electrical connection 46. The control processor 35 may generate a control signal and provide the control signal to the filtering device 44 to switch the filtering device from a first on mode to a second off mode. The control signal controlling the operation of the filtering device may be generated in response to the sensor 28 sensing that at least one environmental characteristic has reached a threshold level indicating that operational mode of the breathing apparatus 10' should change from the first mode of operation to the second mode of operation.

The third electrical connection 46 may extend along a length of the breathing tube 26 as indicated by the electrical connection labeled with reference numeral 47. Thus, control processor 35 may selectively provide data contained in the control signal to an indicator 48 via the third electrical connection 46, 47. The indicator 48 may be selectively mounted onto or within a wearable mask providing the user wearing the mask with a visual indicator describing a particular condition. The control signal may selectively communicate data representing at least one of the (a) sensed environmental characteristic; (b) an current operational mode of the apparatus and (c) information associated with the source of compressed air 12. This data may be selectively displayed to a user via the indicator to provide additional information to the user. In one embodiment, the indicator 48 may be a light emitting diode (LED) able to selectively be illuminated in different colors, wherein a particular color is associated with a particular type of data being communicated. In another embodiment, the indicator 48 may include a plurality of different LEDs having different colors thereby enabling the user to be made aware of multiple different types of information at the same time.

The breathing apparatus 10' may further include a pressure transducer 42 coupled between the pressure reducer 13 on the dispensing valve 14 of the source of compressed air 12 and the control processor 35 in the electronics housing 34. The pressure transducer 42 advantageously senses pressure data associated with the source of compressed air 12. The sensed pressure data is provided via a fourth electrical connection 45 to the control processor in the electronics housing 34. Pressure data sensed by the pressure transducer may be provided via the third and fourth electrical connections 46 and 47, respectively for receipt by the indicator 48. In one embodiment, the pressure transducer may selectively sense that the pressure in the source of compressed air has fallen below a threshold pressure and the control processor may generate a control signal that causes the indicator to be illuminated in a particular manner to notify the user of the breathing apparatus 10' that the pressure level in the source 12 is below the threshold level.

While the embodiments describing the breathing apparatus 10 and 10' shown in FIGS. 1 and 2, respectively include certain different elements and features, one skilled in the art will appreciate that a single embodiment including any or all of the elements described herein may be employed because the breathing apparatus will be able to automatically switch the operational mode from a first negative pressure mode to a second positive pressure mode despite the various sensors and components included therebetween. The breathing apparatus advantageously uses the sensor to sense environmental characteristics in order to control the operation of the pilot valve to open and automatically and immediately supply air from the source 12 to the LDV 24. Additionally, the compressed air provided to the LDV is used to compress a spring and increase an amount of force applied to an exhalation valve of a mask and enable the breathing apparatus to operate in positive pressure mode until such a time that compressed air is at least one of turned off or depleted.

The following FIGS. 3-16 describe in further detail certain individual elements of the breathing apparatus 10. While referred to using reference numeral 10, one skilled in the art will appreciate that reference is also being made to commonly labeled elements in the embodiments 10 and 10' shown in FIGS. 1 and 2, respectively.

Figure 3:
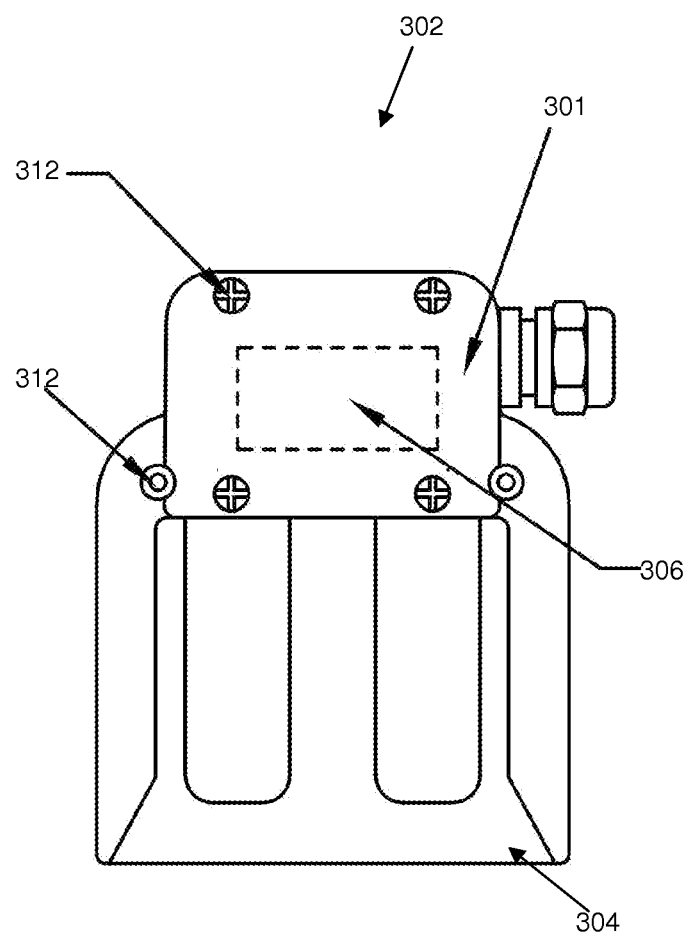
FIG. 3 is a rear view of an adapter for connecting a sensor to the breathing apparatus according to invention principles.

FIG. 3 is rear cross-sectional view of the adapter 30 that receives the sensor 28 therein. The adapter 30 includes an adapter housing 302. The adapter housing 302 may include a communication section 301 and sensor chamber 304. The sensor chamber 304 may be substantially cup-shaped and enable the sensor 28 to be selectively received therein. As shown herein, the sensor chamber 304 is formed as an inverted cup. The dimensions of the sensor chamber 304 of the adapter housing 302 are such that sensor 28 able to sense at least one environmental characteristic may be selectively received and secured therein. The adapter housing 302 includes at least one securing mechanism 312 for selectively securing the sensor 28 (not shown in this Figure) within the sensor chamber 304. In one embodiment, the securing mechanism is a screw or other fastener that releasably secures the sensor 28 within the sensor chamber 304 of the adapter housing 302. The securing mechanism 312 may also be a screw or other fastener. The communication section 301 of the adapter housing 302 further includes a receiver 306 that selectively receives data transmitted from the sensor. In one embodiment, the receiver 306 is an IR receiver that selectively receives data wirelessly transmitted from the sensor 28 using an IR frequency. In another embodiment, the receiver 306 may include at least one electrical contact that mates with an electrical contact on the sensor 28 when the sensor 28 is secured within the sensor chamber 304 of the adapter housing 302. The adapter housing 302 further includes a connector 308 that selectively connects the adapter 30 to the electronics enclosure 34 in FIG. 1. The connector 308 provides strain relief on the adapter and is of sufficient diameter and form to enable a wire to be connected between the receiver 306 in the adapter 30 and the electronics enclosure.

Figure 4:
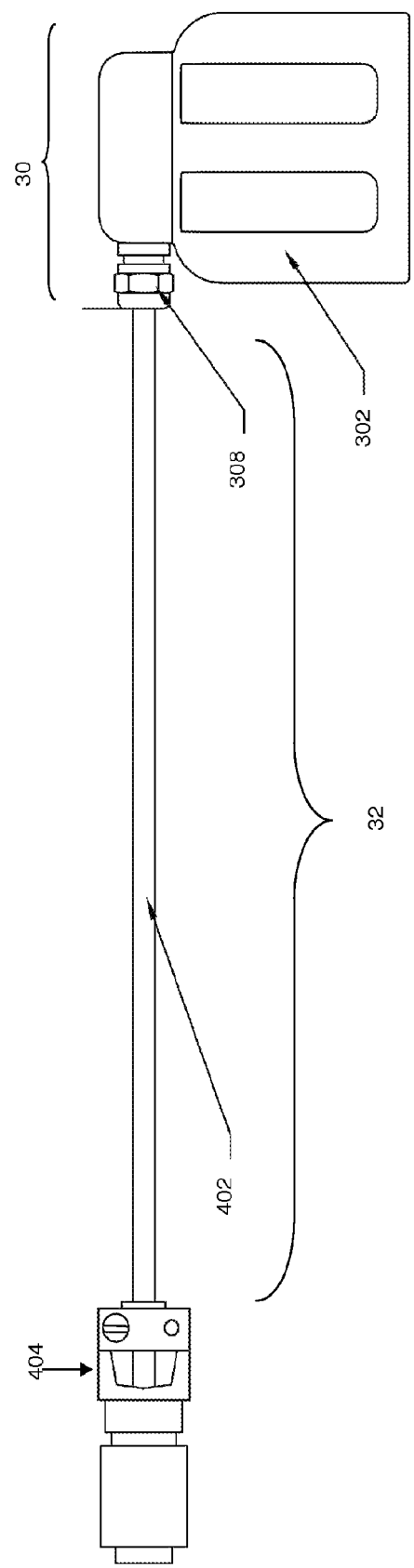
FIG. 4 is an illustrative view of the adapter according to invention principles.

The connection between the adapter 30 and the electronics enclosure 34 is shown in FIG. 4. The connector 308 of the adapter 30 facilitates the second electrical connection 32 between the adapter 30 and the enclosure 34. The second electrical connection may include a cable 402 connected at a first end thereof to the adapter connector 308. A second end of the cable 402, opposite the first end, may be connected to a first input 404 of the electronics enclosure. A wire may originate at the receiver 306 in the adapter 30, passes though the adapter connector (strain relief) 308 and cable 402 and into the electronics enclosure 34 via the first electronics enclosure input 404. Thus, data received by the receiver 306 (FIG. 3) from the sensor 28 may be communicated via the wire in the cable 402 for receipt by the control processor (35 in FIGS. 1 and 2) of the electronics enclosure (34 in FIGS. 1 and 2).

Figure 5:
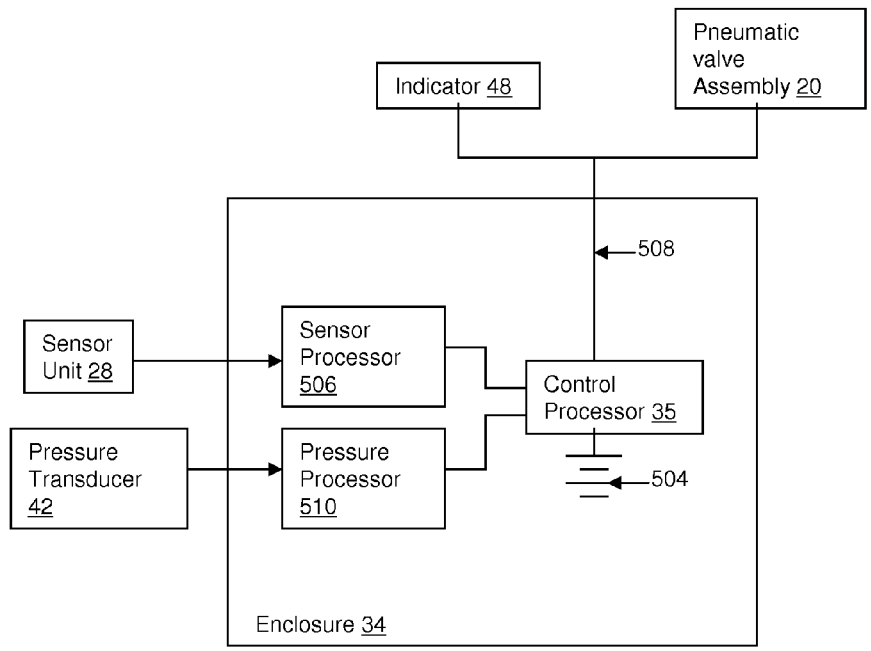
FIG. 5 is an exemplary block diagram of the control device for the breathing apparatus according to invention principles.

FIG. 5 is a block diagram showing the electronics contained within the electronics enclosure 34. The electronics enclosure 34 includes the control processor 35 that is powered by a battery 504. The control processor 35 generates at least one type of control signal to selectively control the operation of a device to which the control processor is connected and a data signal including information received from at least one of a sensor 28 and a pressure transducer 42. In one embodiment, a sensor processor 506 is coupled to the control processor 502. The sensor processor 506 may selectively receive data representing at least one environmental characteristic sensed by sensor 28. Upon receiving the sensed data, the sensor processor 506 compares the sensed data associated with the at least one environmental characteristic to a reference value to determine if the sensed environmental characteristic is one of below the reference value or greater than the reference value. Depending on the environmental characteristic sensed, being below or above the reference value may be indicative of an alarm condition. In response to determining an alarm condition exists, the control processor 502 automatically generates a control signal 508 that is provided to the pilot valve assembly 20 to change the operational mode thereof. The control signal 508 causes the pilot valve assembly 20 to move from the first closed position to the second open position allowing compressed air to flow therethrough and initiate the process of changing from the first operational mode to the second operational mode. In another embodiment, the control signal 508 may also cause the filter device to be deactivated because, once in the second operational mode, the user is breathing the compressed air from the source of compressed air 12.

In another embodiment, the control processor 502 may obtain information describing the sensed environmental characteristic from the sensor processor 506. The information describing the sensed environmental characteristic may be included with the control signal 508 as a data component. The data component of the control signal 508 may include information controlling how the indicator 48 is to be illuminated. In this embodiment, the control signal 508 may also be provided to the indicator 48 which may be illuminated in accordance with the instructions provided by the control processor 502 and included within the data component of the control signal 508.

In a further embodiment, a pressure processor 510 is provided and coupled to the control processor 502. The pressure processor 510 receives data sensed by the pressure transducer 42 that describes at least one characteristic associated with the source of compressed air 12. The control processor 502 may obtain information about the sensed characteristic associated with the source of compressed air 12 from the pressure processor 510 and may be included with the control signal 508 as a data component. The data component of the control signal 508 may include information controlling how the indicator 48 is to be illuminated. In this embodiment, the control signal 508 may also be provided to the indicator 48 which may be illuminated in accordance with the instructions provided by the control processor 502 and included within the data component of the control signal 508.

Figure 6:
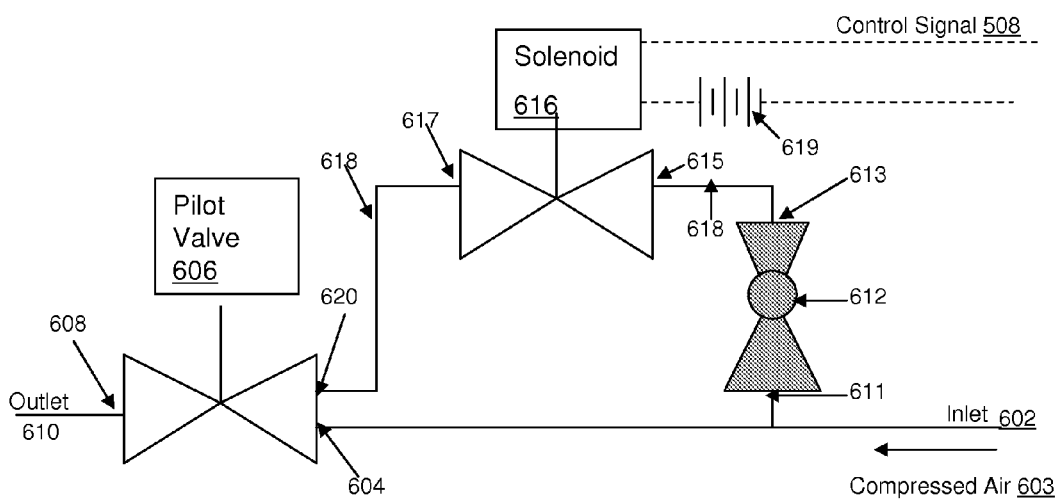
FIG. 6 is an exemplary block diagram of the pneumatic valve assembly of the breathing apparatus according to invention principles.

The use of control signal 508 provided by the control processor 502 to the pilot valve assembly will now be discussed with reference to the schematic diagram in FIG. 6. FIG. 6 includes a schematic diagram of the components contained within the pilot valve assembly 20. The pilot valve assembly 20 includes an inlet 602 for receiving compressed air 603 having a first pressure level. In one embodiment, the compressed air is the medium pressure compressed air having a pressure level substantially equal to 120 psi. The inlet 602 is coupled to a first input port 604 on a pilot valve 606. When the pilot valve is in the second open position the compressed air 603 flows from the inlet, through the first input 604 of the pilot valve 606 and out through the output port 608 of the pilot valve 606, exiting the pilot valve assembly 20 via an outlet 610.

A first pressure reducer 612 includes an input port 611 that receives the compressed air 603. The first pressure reducer 612 receives the compressed air 603 at the input port 611 and reduces the compressed air from the first pressure level to a second pressure level. In one embodiment, the pressure reducer 612 automatically reduces the pressure from the first pressure level (~120 psi) to a second pressure level ranging substantially between 30 and 50 psi. By reducing the pressure of the compressed air 603, the first pressure reducer generates a first pneumatic signal 618 which is output via an output 613 of the first pressure reducer 612.

An input 615 of an electronic solenoid valve 616 is coupled to the output 613 of the first pressure reducer 612 for receiving the first pneumatic signal 618. The electronic solenoid valve 616 may be moveable between a first closed position preventing first pneumatic signal 618 from passing therethrough and a second open position enabling the first pneumatic signal 618 to flow out of an output port 617 of the electronic solenoid valve 616. The electronic solenoid valve 616 is electrically connected to the control processor 502 (FIG. 5) and selectively receives the control signal 508 therefrom. The control signal 508 completes a circuit between the electronic solenoid valve 616 and a power source 619 which causes the solenoid valve to move from a first closed position to a second open position. The output port 617 of the electronic solenoid 616 is coupled to a second input port 620 of the pilot valve 606. The second input port 620 selectively receives the first pneumatic signal 618 and automatically causes the pilot valve 606 to move from the first closed position to the second open position in response to receiving the first pneumatic signal 618 and allowing the compressed air 603 entering the pilot valve assembly 20 at the inlet 602 to flow through the pilot valve 606 and out via the outlet 610.

In the first mode of operation, the compressed air 603 is received at the inlet but is prevented from flowing through the outlet because the pilot valve 606 is in the first closed position. The compressed air 603 is also provided to the first pressure reducer 612 which generates the first pneumatic signal 618. However, the first pneumatic signal 618 is similarly prevented from entering the second input port 620 if the pilot valve is in the first closed position because the electronic solenoid 616 is in the first closed position. In response to detecting an alarm condition sensed by the sensor 28, the control processor 35 (FIG. 5) determines that the breathing apparatus 10 should change from the first mode of operation to the second mode of operation. The control processor (35 in FIG. 5) generates and provides the control signal 508 to the solenoid 616 causing the solenoid valve 616 to move from the first closed position into the second open position allowing the first pneumatic signal 618 to flow into the second input port 620 of the pilot valve 606. The first pneumatic signal 618 causes the pilot valve 606 to move from the first closed position to the second open position thereby initiating the second operational mode and allowing the compressed air 603 at the first pressure level to flow out from the outlet 610 of the pilot valve assembly and into the LDV 24 (or PAPR) and mask being worn by the user.

Figure 7:
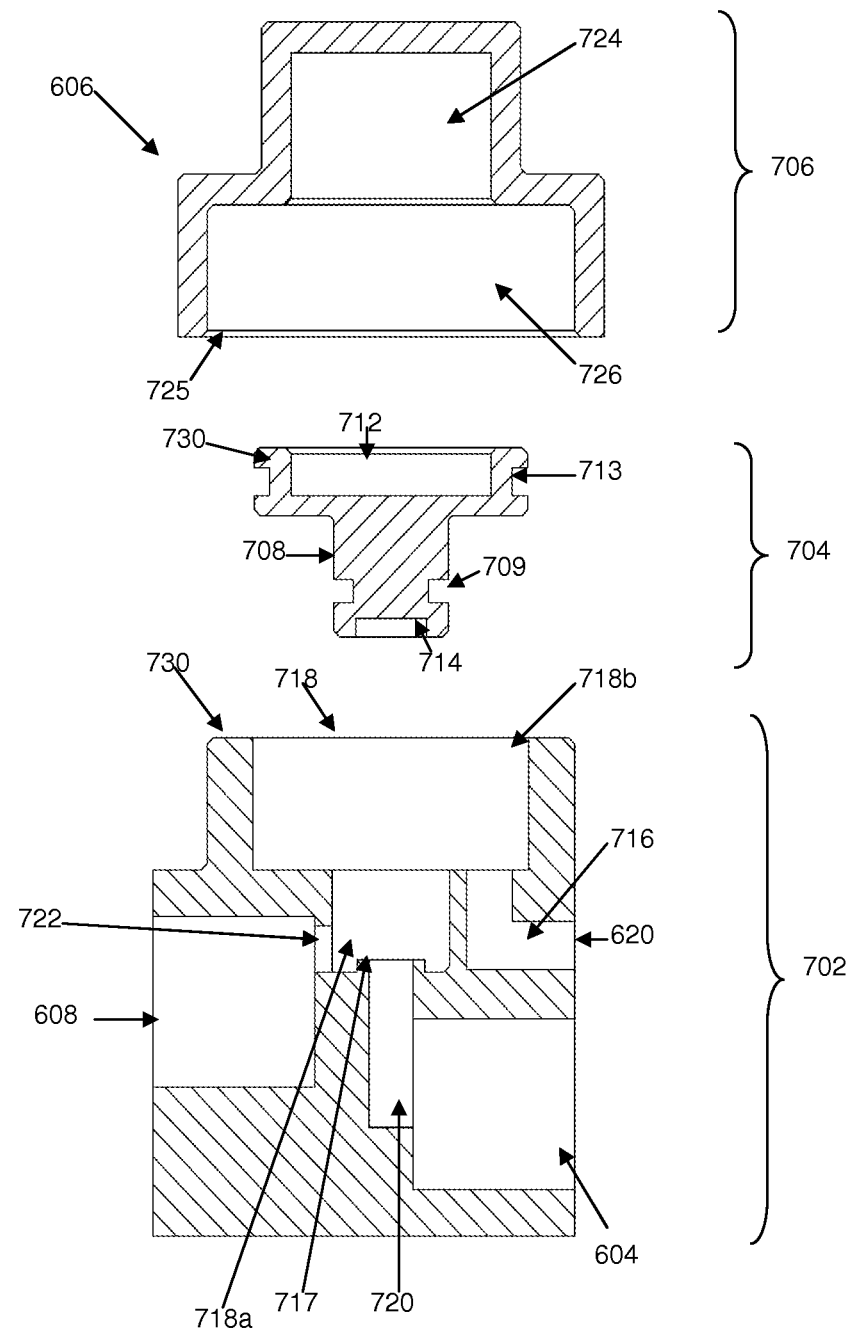
FIG. 7 is an exploded cross-sectional view of the pneumatic valve of the pneumatic valve assembly according to invention principles.

FIG. 7 is an exploded cross-sectional view of the pilot valve 606 shown in FIG. 6. The pilot valve 606 includes a valve body 702, a piston 704 and a cap 706. Also included but not shown in this figure is a spring (802 in FIG. 8) positioned between the piston 704 and the cap 706.

The piston 704 includes a head section 710 and a stem section 708 extending from an underside of the head section. The head section 710 includes a first notch 713 extending around a circumference thereof. The first notch 713 is able to selectively receive a sealing device (e.g. an O-ring) therein at least partially creating a seal between the piston 704 and the body 702 of the valve 606. The head section 710 further includes a first recess 712 for receiving an end of the spring (802 in FIG. 8) therein.

The stem section 708 includes a second notch 709 extending around a circumference of the piston 704 at a predetermined distance from an end of the piston 704 and on a side of the stem section 708 opposite the connection to the head section 710. The second notch 709 also selectively receives a further sealing device therein creating at least a partial seal between the stem 708 of the piston 704 and the body 702 of the valve 606. The end of the stem section 708 opposite the connection to the head section 710 includes a second recess 714 for receiving a further sealing device therein.

The valve body 702 includes the first input port 604 connected to the inlet 602 of the pilot valve assembly 20 for receiving compressed gas at the first pressure level. The valve body 702 also includes the second input port 620 coupled to the output of the solenoid valve (616 in FIG. 6) for receiving the first pneumatic signal therein. The valve body 702 includes a signal channel 716 connecting the second input port 620 with a piston receptacle 718. The piston receptacle is a compartment extending into the valve body 702 having a shape substantially similar to the shape of the piston 704. The piston receptacle 718 includes a first compartment 718a having a diameter able to accommodate the stem section 708 of the piston 704 and a second compartment 718b having a diameter to accommodate the head section 710 of the piston 704. Additionally, a central channel 720 couples the first input port 604 to the first compartment 718a of piston receptacle 718. A protrusion 717 extends upward from a base of the first compartment 718 and surrounds an opening of the central channel 720. The first compartment 718a of the piston receptacle 718 is further coupled to the output port 608 by an output channel 722.

The cap 706 includes a cap recess 725 having a first cap compartment 724 and a second cap compartment 726. The first cap compartment 724 has a diameter substantially equal to a diameter of the recess 712 in the head section 710 of the piston 704 and smaller than the head section 710. The second compartment 726 has a diameter substantially equal to a diameter of the head section 710 of the piston 704. The cap recess 725 should be shaped such that the head section 710 of the piston 704 does not enter the first compartment 724 of the cap recess 725. Specifically, the first compartment 724 and the recess 712 of the head section 710 of the piston 704 have a diameter able to accommodate a spring that can selectively provide enough tension to maintain the piston 704 within the piston receptacle 718.

Upon assembly, the stem section 708 and head section 710 of the piston 704 are received within the first and second compartment 718a and 718b, respectively of the valve body 702 and the cap 706 is positioned over a top end 730 of the valve body 702 creating a hermetic seal therebetween.

Figure 8:
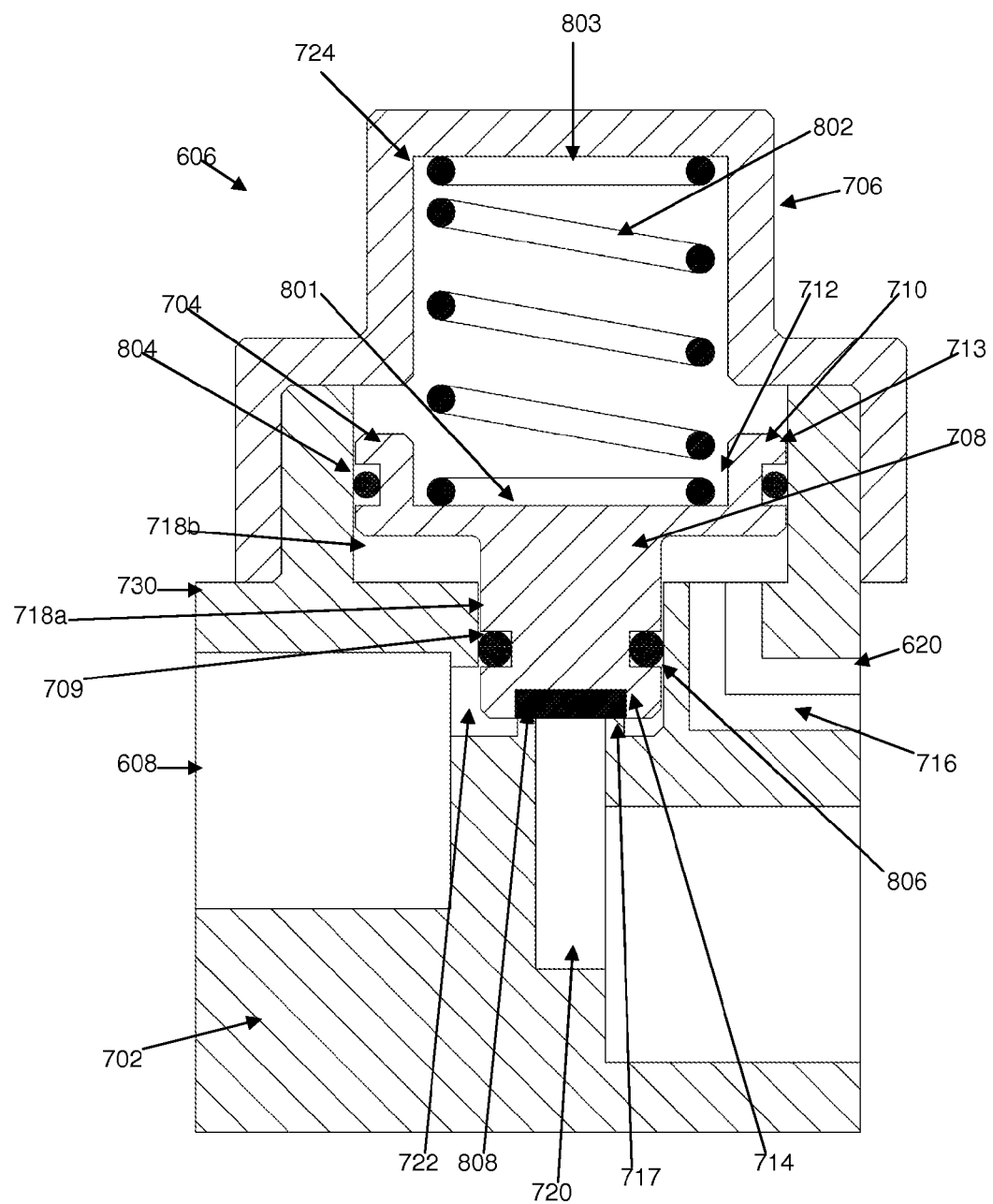
FIG. 8 is a cross-sectional view of the pneumatic valve of the pneumatic valve assembly according to invention principles.

The operation of the pilot valve 606 will now be discussed with respect to FIG. 8. FIG. 8 is a cross section of the pilot valve 606 in an assembled state and includes similar structures and elements as described above with respect to FIG. 7, discussion of which will not be repeated herein. FIG. 8 also includes the spring 802 having a first end 801 received within the first recess 712 of the head section 710 of the piston 704 and a second end 803 received within the first compartment 724 of the cap recess 725. FIG. 8 further shows a first sealing device 804 received within the first notch 713 in the head section 710 of the piston 704. In one embodiment, the first sealing device 804 may be a polymer based O-ring that creates at least a partial seal between the head section 710 and a wall of the second compartment 718b of the piston receptacle 718. A second sealing device 806 is received within the second notch 709 of the stem section 708 and creates at least a partial seal between the stem section 708 and a wall of the first compartment 718a of the piston receptacle 718. A third sealing device 808 is positioned within the second recess 714 on the base of the stem section 708. The third sealing device 808 creates at least a partial seal between the protrusion 717 surrounding the central channel 720. The at least partial seal created between the protrusion 717 and the stem 708 selectively seals the central channel 720 from the output channel 722.

In the first mode of operation, the pilot valve 606 is in the first closed position. The spring 802 is in an uncompressed state and exerts an amount of force on the head section 710 of the piston 704 to maintain the stem 708 of the piston 704 within the first compartment 718a of the piston receptacle 718. In this position the third sealing device 808 seals off access between the central channel 720 and the output channel 722. Additionally, upon creating a seal, a gap 810 is maintained between an underside of the head section 710 of the piston 704 and the walls of the second compartment 718b of the piston receptacle 718. The force exerted by the spring 802 on the piston 704 is sufficient to prevent compressed air at the first pressure level entering the central channel 720 via the input port 604 from displacing the piston 704 and compressing the spring 802. This occurs because the surface area over which the pressure from the compressed air acts is insufficient to cause the spring 802 to be compressed.

In the second mode of operation, the first pneumatic pressure signal is received at the second input port 620 and flows via the signal channel 716 into the gap 810 between the piston head 710 and the second compartment 718b. The first pneumatic pressure signal flows around the stem 708 and exerts a force on the underside of the piston head 710 sufficient to at least partially compress the spring 802 and unseat the stem 708 from within the first compartment 718a. This will enable passage of compressed air from the central channel 720 to the output channel 722 thereby connecting the first input port 604 with the output port 608 enabling compressed air having a first pressure level to flow therethrough.

Upon receipt of the first pneumatic signal which causes the spring 802 to be compressed, the pilot valve 606 will remain in an open state until the source of compressed air 12 is turned off or is depleted to a certain level. This will reduce the force applied to the spring 802 by the piston 704 and allow the spring 802 to return to the uncompressed state. In one embodiment, the valve 606 may move from the second open position back to the first closed position by manually turning off the source 12 of compressed air. In another embodiment, the source of compressed air may be automatically shut down via a control signal.

Figure 9A:
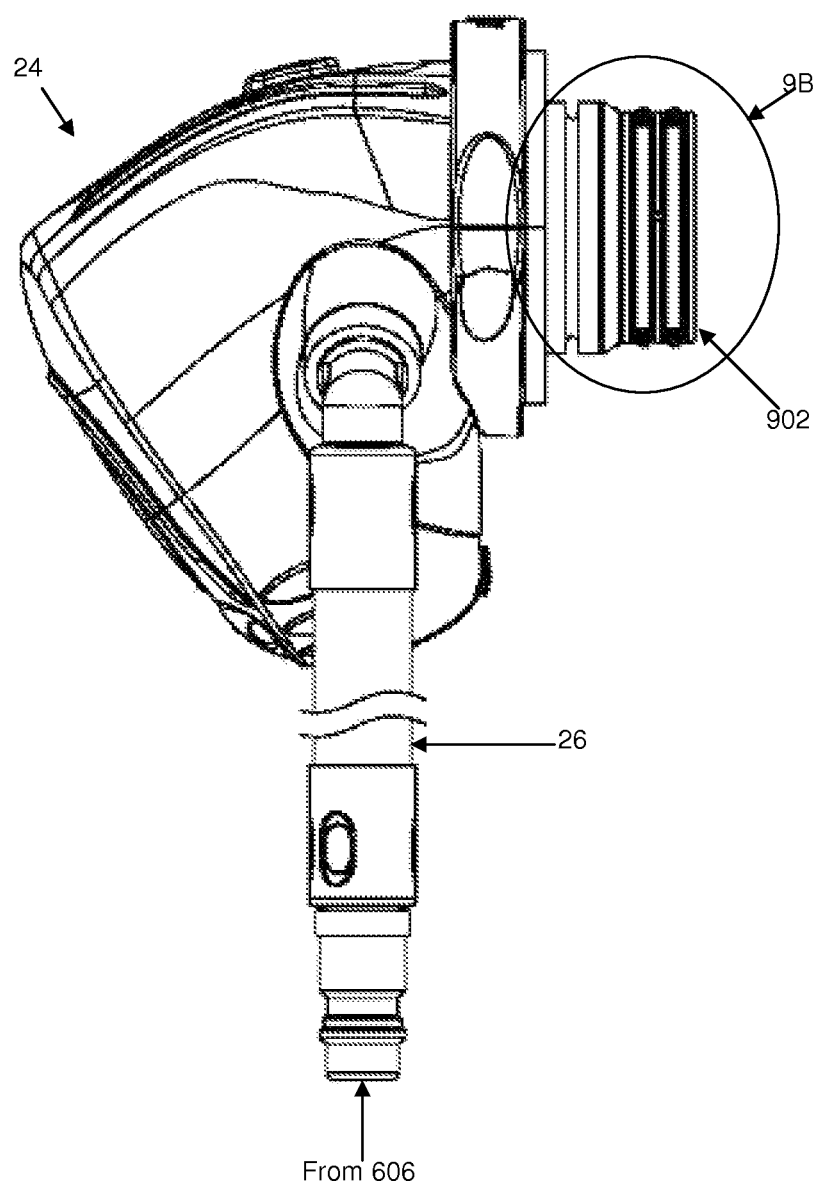
FIG. 9A is a side view of a lung demand valve for use with the breathing apparatus according to invention principles.
Figure 9B:
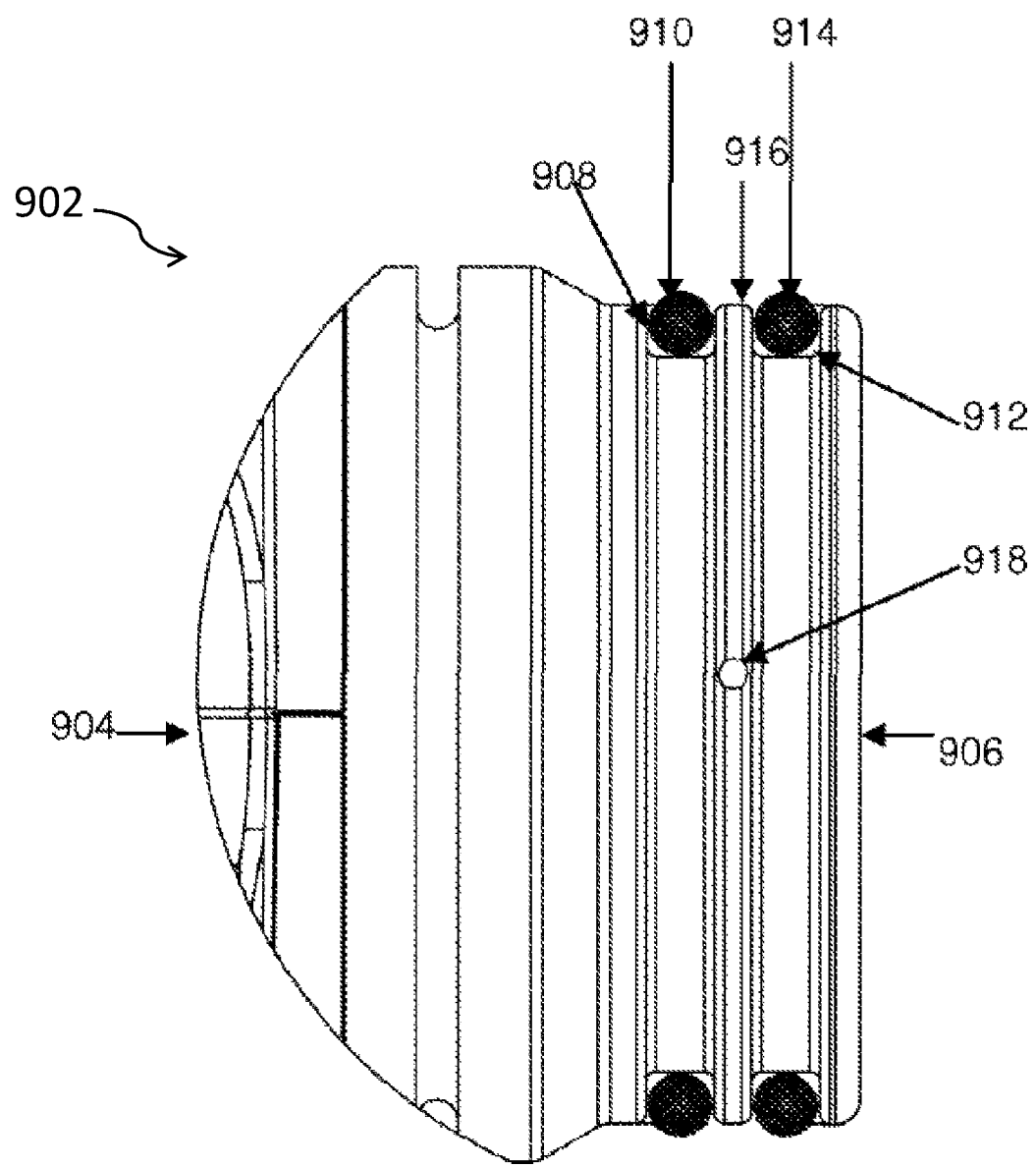
FIG. 9B is an detailed view of the connector of a lung demand valve shown in the circle labeled 9B in FIG. 9A according to invention principles.

Once the pilot valve 606 has moved from the first closed position into the second open position, the second mode of operation is initiated. Compressed air flows from the output port 608 of the valve and out through the outlet 610 of the pilot valve assembly. The compressed air further flows through a breathing tube 26 into a lung demand valve 24 (LDV) as shown in FIGS. 9A and 9B. The LDV 24 in FIG. 9A may include similar components as a conventional LDV with one important modification. The LDV 24 used with the breathing apparatus 10 advantageously includes an operational mode switch contained therein that generates a second pneumatic signal for controlling the operation of certain components in the mask to change the operational mode from a first negative pressure mode to a second positive pressure mode. The operational mode switch will be discussed hereinafter with respect to FIGS. 11 and 12. Additionally, the LDV 24 includes a modified mask connector 902 able to selectively communicate the second pneumatic signal generated by the operational mode switch to the components in the mask. An enlarged depiction of the mask connector 902 is shown in FIG. 9B.

The LDV 24 includes the mask connector 902 as shown in FIG. 9B for connecting a mask thereto. The mask connector 902 includes a first end 904 and a second end 906 opposite the first end 904. The second end 906 is selectively received by an LDV input port of a mask (see FIGS. 13-15) The second end 906 includes a first notch 908 extending around a perimeter of the connector 902 and is positioned proximate the first end 904 of the connector 902. The first notch 908 includes a first sealing device 910 (e.g. O-ring) retained therein. The second end 906 includes a second notch 912 extending around a perimeter of the connector 902 and is positioned between the first notch 908 and the second end 906 of the connector 902. The second notch 912 includes a second sealing device 914 (e.g. O-ring) retained therein.

A gap 916 is positioned between the first and second notches 908 and 912 respectively. The first and second sealing devices 910 and 914 positioned in the first and second notches 908 and 912 seal the gap 916. A signal output port 918 is positioned within the gap 916. The second pneumatic signal passes through the signal output port 918 and is received within the gap 916. When the mask is positioned on the connector 902, the second pneumatic signal is provided to a signal input port (1218 in FIGS. 12-15) of the mask. Thus, by positioning the output port 918 in the gap 916, the mask connector 902 advantageously provides a manner for isolating a pneumatic signal enabling communication of the pneumatic signal between the LDV 24 and certain components of the mask. Moreover, as the signal is pneumatic and is isolated between the sealing devices 910 and 914 in the first and second notches 908 and 912, the signal output port 918 on the mask connector 902 advantageously does not need to be aligned with the a corresponding signal input port on the mask. Rather, the pneumatic signal will simply flow out from the signal output port 918 and remain trapped between the sealing devices until it is received at a signal input port on the mask. Thus the mask connector 902 advantageously provides the user with a greater degree of mobility without having to worry about the operational mode of the breathing apparatus. More specifically, the present configuration advantageously enables the mask to rotate freely about the mask connector while still maintaining signal communication between the LDV and the mask. The gap 916 in which the second pneumatic signal is trapped advantageously enables this free rotation of the mask about the mask connector 902.

Figure 10:
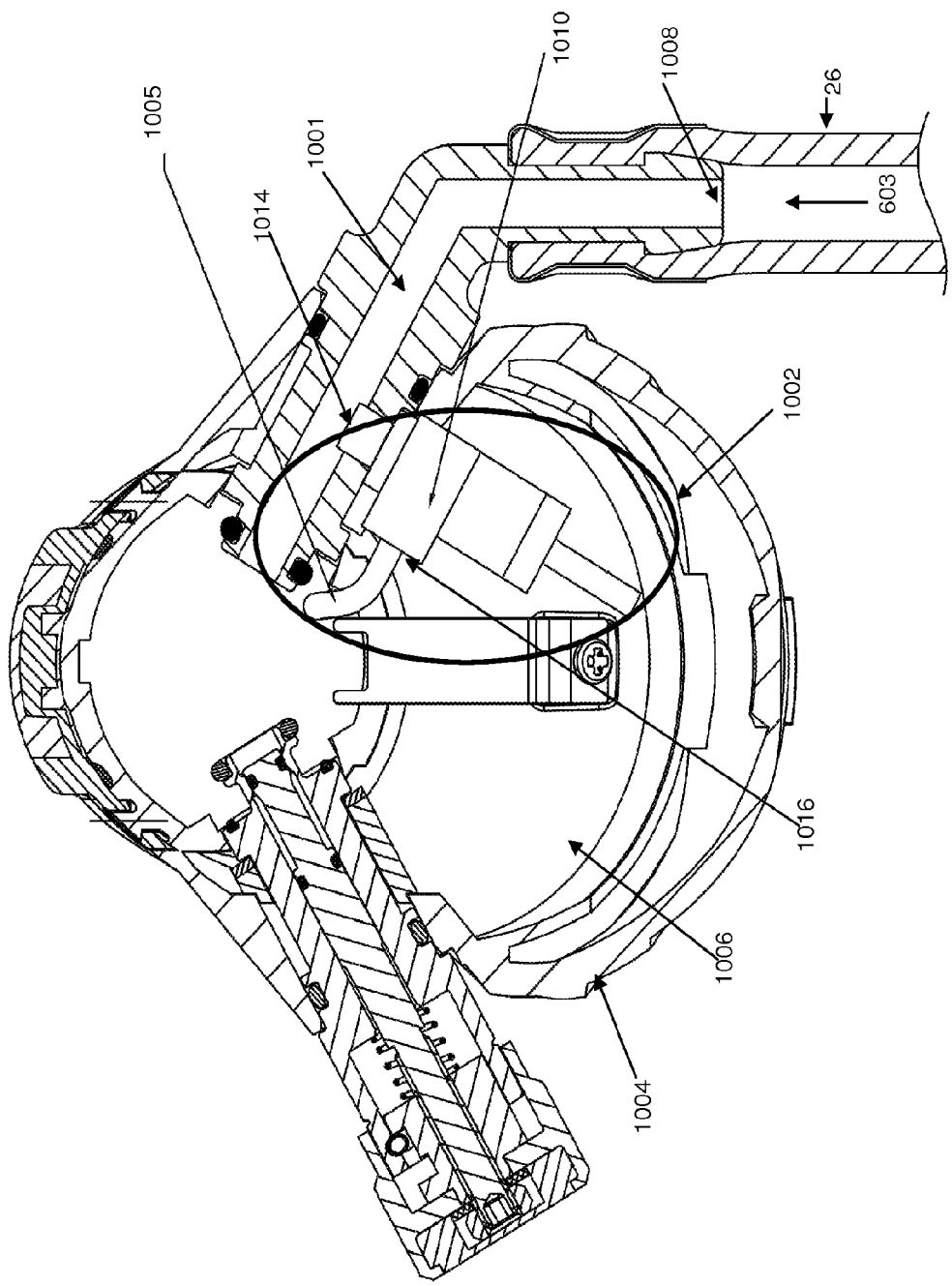
FIG. 10 is a cross sectional view of the lung demand valve for use with the breathing apparatus according to invention principles.
Figure 11:
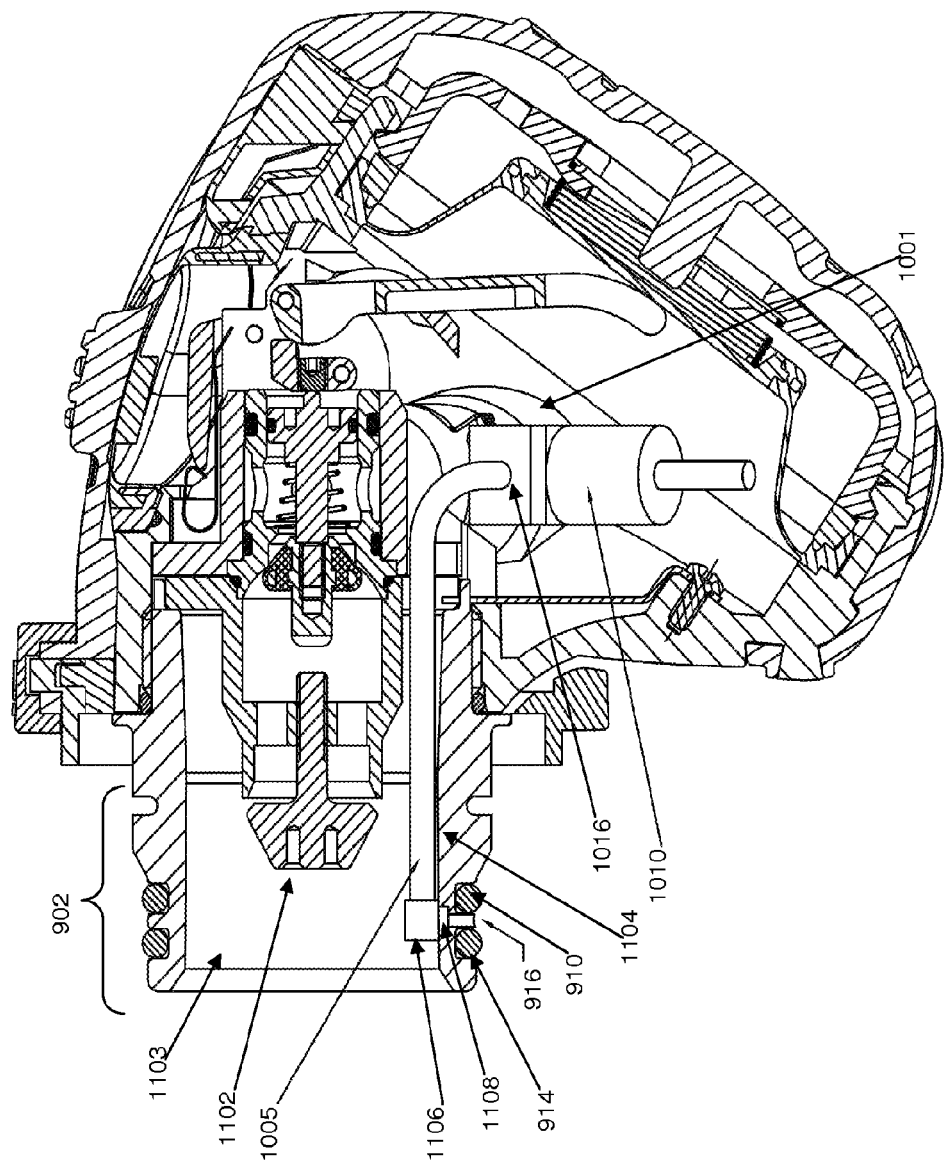
FIG. 11 is a cross sectional view of the lung demand valve for use with the breathing apparatus according to invention principles.

FIGS. 10 and 11 illustrate the mode operational switch 1002 connected in the LDV which generates the second pneumatic signal that is provided via the signal output port 918 shown in FIG. 9. FIG. 10 is a cross section of an underside of an LDV 24 including the mode operational switch 1002. The LDV 24 includes a housing 1004 having a compartment 1006 therein. This cross sectional view is of an LDV having a rear cover and diaphragm removed therefrom. The breathing tube 26 is connected at an input port 1008 of the LDV 24. The input port 1008 includes a channel 1001 through which compressed air 603 flows. The compressed air flowing through the channel 1001 is provided to a regulator that decreases the compressed air from the first pressure level to a third pressure level, the third pressure level being a breathable pressure level, in a known manner.

The mode operational switch 1002 is positioned within the compartment 1006 and is oriented on a side of the diaphragm opposite the housing 1004. The mode operational switch 1002 includes a second pressure reducer 1010, similar to the first pressure reducer used in the pilot valve assembly 20. The second pressure reducer 1010 selectively generates the second pneumatic signal as follows. An input 1012 of the second pressure reducer 1010 is connected to a channel 1001 through which compressed air 603 flows. Compressed air 603 is siphoned off by the second pressure reducer 1010 through the input 1014. The second pressure reducer 1010 reduces the pressure of compressed air 603 to the second pressure level (e.g. ranging between 30 and 50 psi) thereby generating the second pneumatic signal. The second pneumatic signal is output by the second pressure reducer 1010 into a signal channel 1005 that is coupled thereto. The signal channel 1005 further connects the second pressure reducer 1010 with the signal output port 918 in the mask connector 902 (as shown in FIGS. 9A and 9B).

The path of the signal channel 1005 connecting the second pressure reducer 1010 with the signal output port 918

(FIGS. 9A & 9B) is shown in FIG. 11. FIG. 11 is a side cross sectional view of the LDV shown in FIG. 9. As shown herein the channel 1001 is shown feeding a conventional regulator 1102 used in LDV's to step down a pressure of compressed air from a medium pressure (e.g. 120 psi) to a breathable pressure. The regulator 1102 extends from within the LDV housing 1004 into the mask connector 902. The mask connector 902 is substantially cylindrical in shape and includes an inner channel 1103 into which the regulator 1102 extends. The inner channel 1103 includes a channel wall 1104. The channel wall 1104 includes an aperture 1108 extending through the channel wall and positioned between the notches 908 and 912 having respective sealing devices 910 and 914 contained therein. The aperture 1108 is aligned with the signal gap 916 on an exterior surface of the mask connector 902. The signal channel 1005 extends from the output port 1016 on the second pressure reducer 1010 extends into the inner channel 1103 of the mask connector 902 and along the channel wall 1104 thereof. A right angle connector 1106 is connected at an end of the signal channel 1005 opposite the connection to the output port 1016. The right angle connector 1106 is further aligned with the aperture 1108 which forms the signal output port 918.

In operation, compressed air having the first pressure is provided via the breathing tube to the channel 1001 in the housing 1004 of the LDV 24. The compressed air is received at the input port 1014 of the second pressure reducer 1010 which generates the second pneumatic signal and provides the second pneumatic signal through the signal channel 1005 for output via the signal output port 918 into the signal gap 916 for receipt by the mask being worn by the user.

Figure 12:
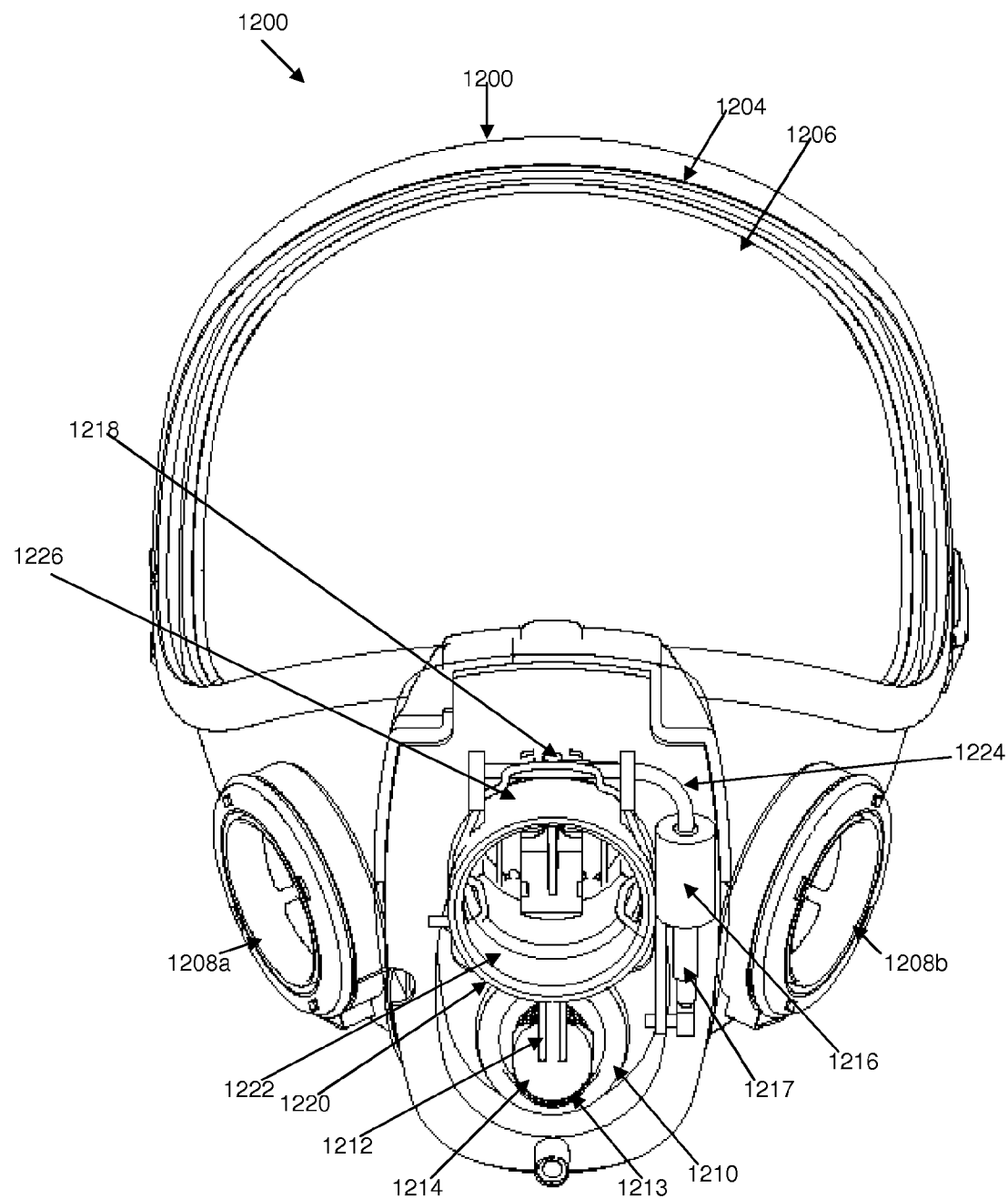
FIG. 12 is a front view of a mask shown without a cover for use with the breathing apparatus according to invention principles.

An exemplary mask enabling automatic switching between the first negative pressure mode and second positive pressure mode is shown in FIGS. 12-16. FIG. 12 is a front view of a face mask 1200 for use with the breathing apparatus 10. The mask 1200 includes a housing 1202 having an aperture 1204 for receiving faceplate 1206 therein. The faceplate 1206 enables the user to have full view of their surroundings in all conditions. The mask housing 1202 further includes a first access port 1208a and a second access port 1208b. The first and second access ports 1208a and 1208b enable a user to selectively connect a filtration device such as an APR or a PAPR thereto for use during the first mode of operation where the breathing apparatus is operating in negative pressure mode. The remaining elements of the housing 1202 will not be further described as the features are similar to those found on full facemasks 1200 used in SCBA configurations.

The mask 1200 includes an LDV connection section 1208 that enables an LDV 24 to be releasably connected to the mask 1200 via an LDV connection port 1220. The LDV connection port 1220 includes an inner wall 1222. A seal is formed by the first and second sealing devices 910 and 914 in the mask connector 902 of the LDV 24. The LDV connection port 1220 further includes a signal input port 1218 extending therethrough. The LDV connection port 1220 receives the mask connector 902 of the LDV and releasably secures the LDV 24 to the mask 1200. Upon connection of the LDV 24 with the mask 1200 via the LDV connection port 1220, the signal input port 1218 is aligned with the gap 916 on the mask connector 902 received within the LDV connection port 1220. This enables the first and second sealing devices 910 and 914 in the mask connector 902 to form a seal between the mask connector 902 and the inner wall 1222 thereby isolating the second pneumatic signal within the gap 916 and enabling the second pneumatic signal to be received via the signal input port 1218 on the mask 1200. The LDV connection section 1208 includes a signal channel 1224 mounted thereon connecting the signal input port 1218 on the mask with a pneumatic actuator 1216. The pneumatic actuator 1216 is connected to a bridge assembly 1212 that can selectively compress an exhalation valve spring 1213 of the mask 1200 using a tab 1214. The tab 1214 is connected to the exhalation valve 1210 via the spring 1213 that, when uncompressed, exerts a minimal force against the exhalation valve 1210. The exhalation valve 1210 may be a rubber disc that, in the first mode of operation (negative pressure mode) is maintained in a selectively closed position by a force exerted by the exhalation valve spring 1213 in the uncompressed state. When a user exhales, the force of the air being exhaled is sufficient to displace the exhalation valve and allow air to escape. In the mask was to remain in the first mode of operation when compressed air is being provided from the source, the force exerted by the compressed air would cause the exhalation valve to remain open and allow the compressed air to continually escape. Thus, the transition from first operational mode to second operational mode is required as discussed below.

The bridge assembly 1212 is pivotally connected to the LDV connection section 1208 on opposing sides of the LDV connection port 1220. The pneumatic actuator 1216 includes an arm 1217 that selectively extends upon actuation thereof. The arm 1217 is connected to the bridge assembly 1212 and, upon actuation of the actuator 1216, the arm 1217 is caused to extend and the bridge assembly is caused to pivot and rotate in a direction compressing the spring 1213 against the exhalation valve 1210. By compressing the spring 1213, the operational mode of the mask 1200 is changed from the first operational mode to the second operational mode. The ability of the compressed air flowing into the mask 1200 via the LDV from escaping through the exhalation valve 1210 is reduced (or prevented) and the mask 1200 is caused to have a positive pressure therein. The positive pressure state within the mask 1200 automatically flushes out any contaminates that inadvertently enter the mask 1200, if any leak were to occur. In particular, by compressing the exhalation valve spring 1213 against the exhalation valve an increased resistance is applied to the air attempting to flow out from the exhalation valve. Thus, the exhalation valve may still be displaced but the force required to displace the exhalation valve is greater than a force applied to the exhalation valve 1210 by the spring 1213. This advantageously enables a user to exhale and have the exhaled gas escape while maintaining a positive pressure in the mask and preventing the unintentional leakage of compressed air from the source of compressed air.

Figure 13:
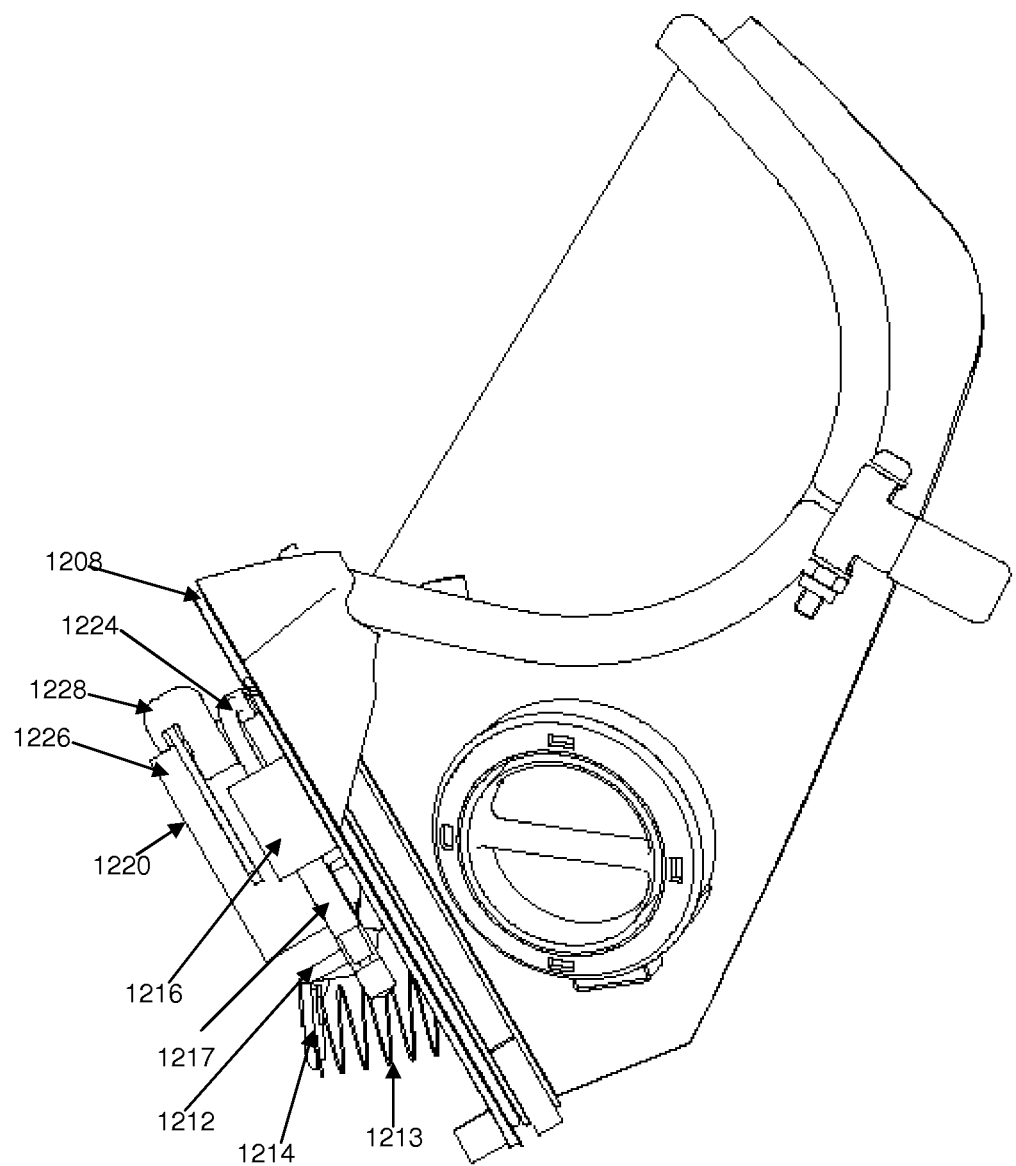
FIG. 13 is a side view of a mask shown without a cover for use with the breathing apparatus according to invention principles.

FIG. 13 is a side view of the mask 1200 shown in FIG. 12. The LDV connection port 1220 extends outward from the LDV connection section 1208. A securing mechanism 1228 is positioned on the exterior surface of the LDV connection port 1220 for releasably securing the LDV within the connection port 1220. The securing mechanism 1228 may be a spring release mechanism that secures the LDV within the LDV connection port 1220 as is conventionally known. The signal channel 1224 is mounted on the exterior surface 1226 of the LDV connection port 1220 and is positioned between the securing mechanism 1228 and a surface of the LDV connection section 1208. The signal channel 1224 may be connected to the signal input port 1218 using a right angle connector enabling the signal channel 1224 to extend laterally from the signal input port (1218 in FIG. 12) and curve around the LDV connection port 1220 to connect the signal input port 1218 to the pneumatic actuator 1216. The mask 1200 shown in FIG. 13 is in the first operational mode as the spring 1213 positioned between the tab 1214 of the bridge assembly 1212 and exhalation valve 1210 is in the uncompressed state.

Figure 14:
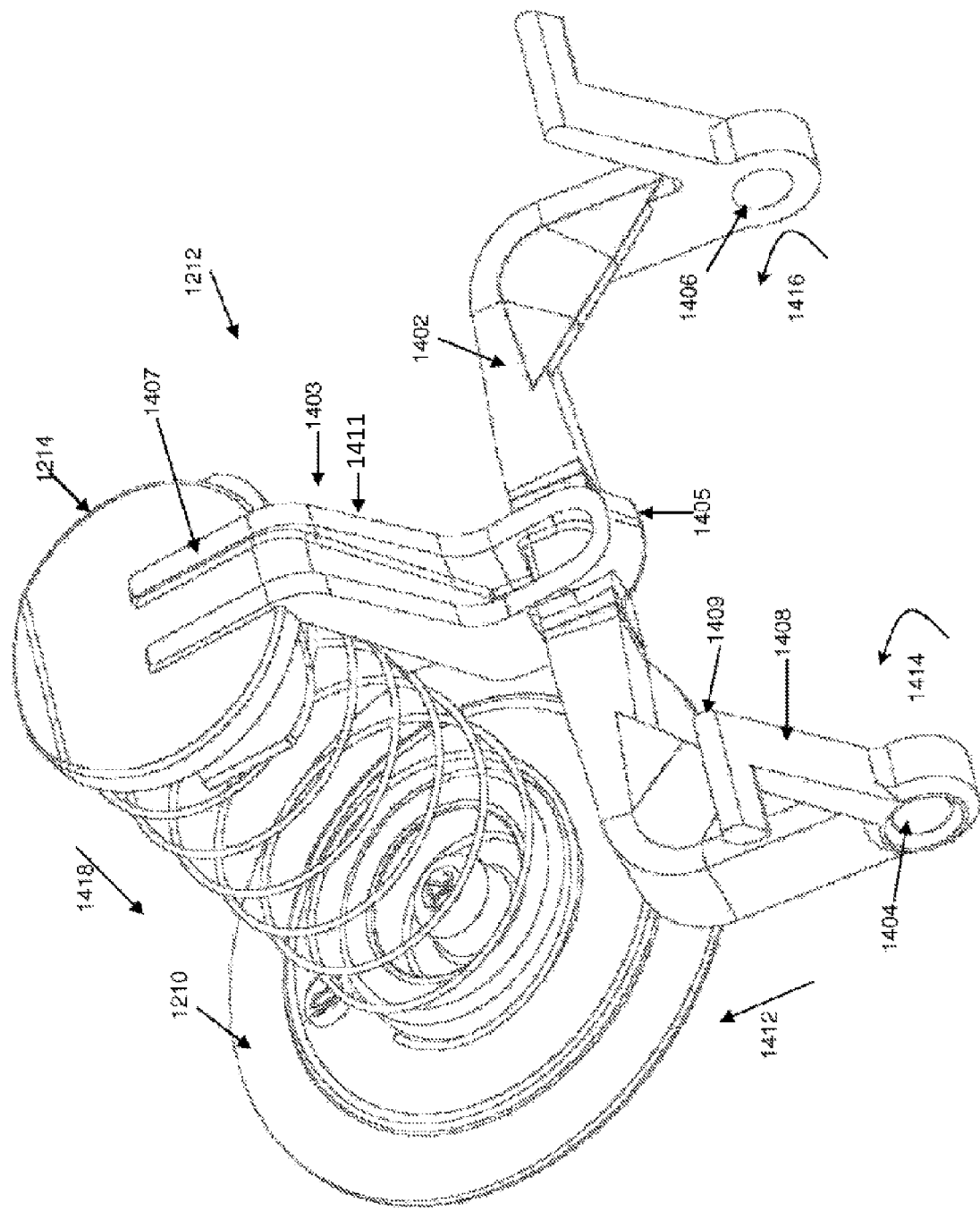
FIG. 14 is a perspective view of a bridge assembly of the mask for use with the breathing apparatus according to invention principles.

FIG. 14 is a perspective view of the bridge assembly 1212 and the connection of the bridge assembly 1212 with the exhalation valve 1210 via the spring 1213. The bridge assembly 1212 is formed from a substantially C-shaped member 1402. The C-shaped member 1402 includes a first end 1404 pivotally connected to a surface of the mask housing (see FIGS. 15 and 16). A second end 1406 of the C-shaped member 1402 opposite the first end 1404 is also pivotally connected to a surface of the mask housing. The C-shaped member 1402 is positioned around the LDV connection port 1220 (FIG. 12) such that the LDV connection port 1220 is positioned substantially at a midpoint between the first end 1404 and the second end 1406. A first arm 1408 extends outward from the first end 1404 of the C-shaped member 1402 at a predetermined angle. A second arm extends outward from the second end 1406 of the C-shaped member 1402 at a predetermined angle. The first arm 1408 includes a connection end 1409 that connects the bridge assembly 1212 to the arm 1217 of the pneumatic actuator 1216. The connection of the bridge assembly 1212 to the arm 1217 of the pneumatic actuator 1216 at the first connection arm is described for purposes of example only and is dependent on the configuration and positioning of the pneumatic actuator 1216 on the mask. Thus, if the pneumatic actuator 1216 was positioned on an opposite side of the LDV connection port 1220 than is shown in FIGS. 12 and 13; the bridge assembly 1212 may be connected to the pneumatic actuator 1216 via the second arm 1410 in a similar manner.

A step shaped member 1403 extends from substantially a midpoint of the C-shaped member 1402. The step shaped member 1403 includes a midsection 1411 that extends upward from a surface of the C-shaped member 1402. A first end 1405 of the step shaped member 1403 connects a first end of the midsection 1411 to the C-shaped member 1402 and a second end 1407 connects an end of the midsection opposite the first end 1405 to the tab 1214.

In operation, the arm 1217 of the pneumatic actuator 1216 extends in a direction indicated by the arrow labeled with reference numeral 1412 causing the first and second ends 1404 and 1406 to pivot in the direction indicated by the arrows labeled 1414 and 1416, respectively. This causes the C-shaped member 1402 to rotate in a direction indicated by the arrow labeled 1418 causing the tab 1214 to compress the spring 1213 and cover the exhalation valve 1210 placing the mask into the second operational mode creating a positive pressure state in the mask 1200.

Figure 15:
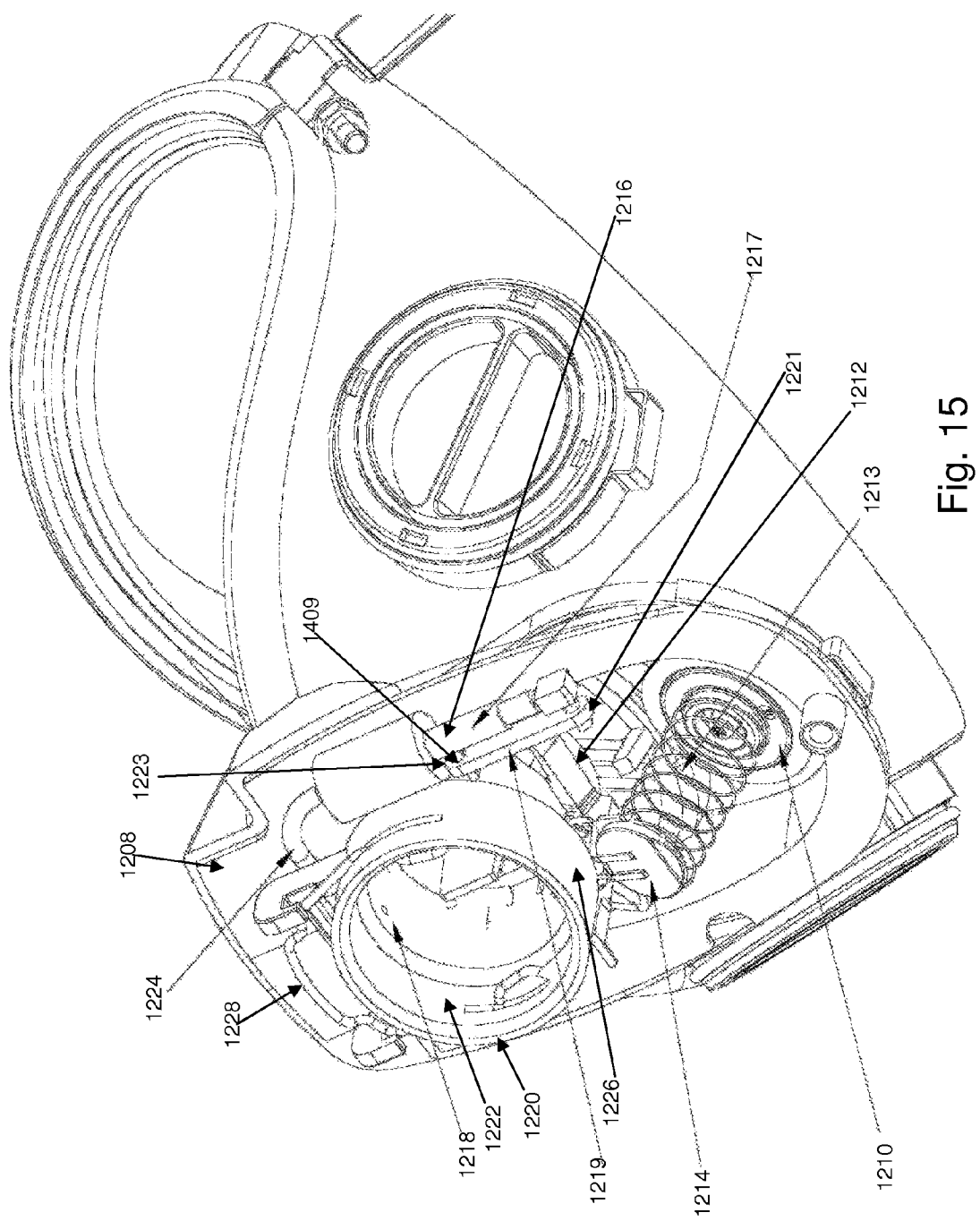
FIG. 15 is a perspective view of a mask shown without a cover operating in the first operational mode according to invention principles.

FIG. 15 is a perspective view of the mask 1200 configured to operate in the first operational mode. The housing 1202 of the mask 1200 includes the LDV connection section 1208. An LDV connection port 1220 has an exterior surface 1226 on which a securing mechanism 1228 is mounted. The LDV connection port 1220 also includes an interior wall 1222 having a signal input port 1218 extending therethrough. An LDV mask connector 902 (FIG. 9) is selectively received within the LDV connection port 1220 and secured by the securing mechanism 1228. Upon securing the LDV mask connector 902 within the LDV connection port 1220 via the securing mechanism 1228, the signal input port 1218 is aligned with one of the signal gap (916 in FIG. 9) and the signal output port (918 in FIG. 9). A seal is formed isolating the signal gap on the mask connector enabling the second pneumatic signal to be received via the signal input port 1218 for selectively configuring the operational mode of the mask 1200.

The signal channel 1224 connects the signal input port 1218 in the LDV connection port 1220 to the pneumatic actuator 1216. The pneumatic actuator 1216 includes an arm 1217 that extends in a direction away from the pneumatic actuator 1216. The arm 1217 is further connected to the first connection end 1409 of the bridge assembly 1212 as described in FIG. 14 by a connection arm 1219. A first end 1221 of the connection arm 1219 is connected to the actuator arm 1217 and a second end 1223 to the first connection end 1409 of the bridge assembly 1212. The pneumatic actuator 1216 selectively receives the second pneumatic signal via the signal channel 1224 and causes the arm 1217 to extend outward and modify the configuration of the mask 1200 from the first negative pressure mode to the second positive pressure mode.

Figure 16:
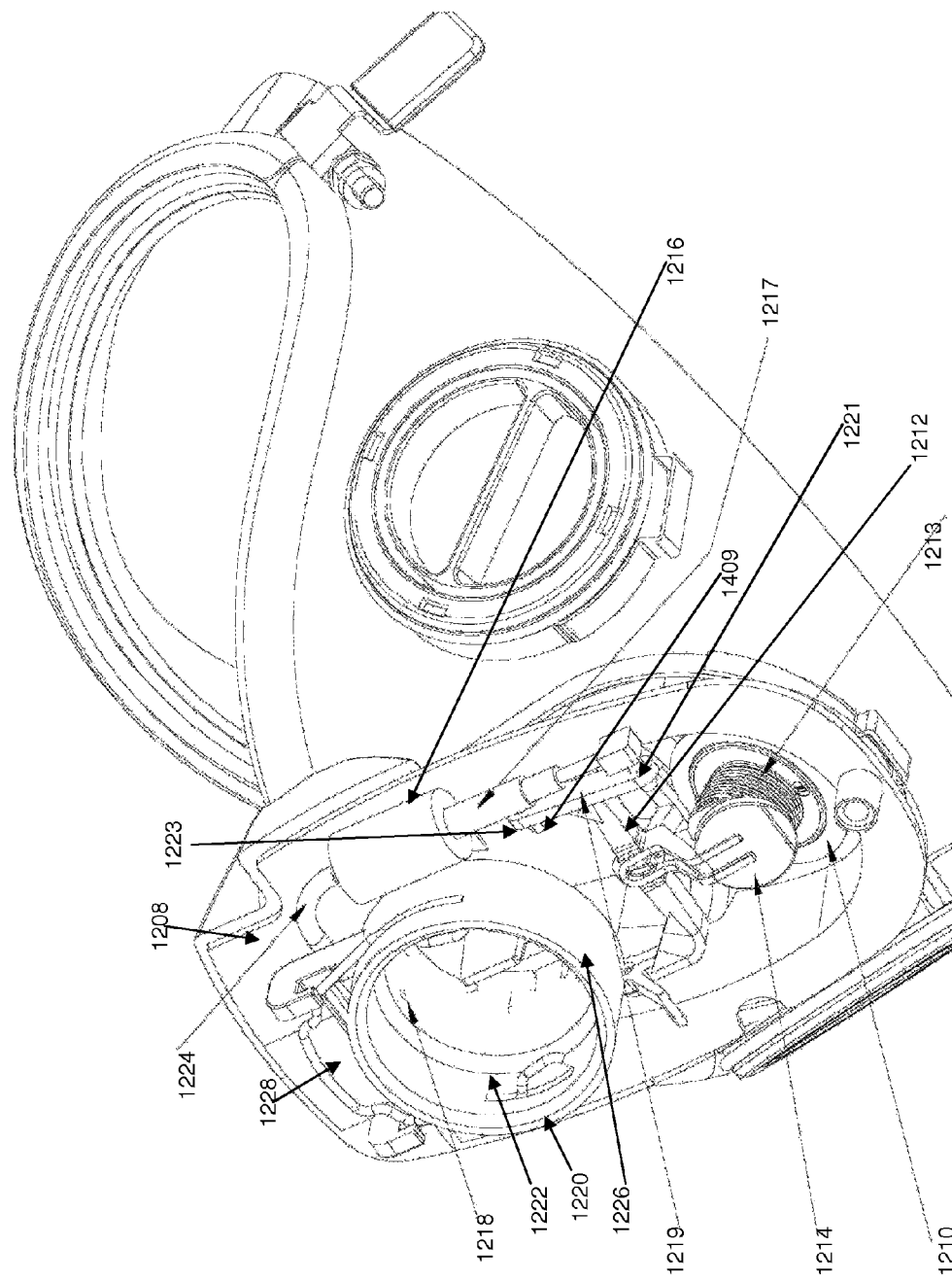
FIG. 16 is a perspective view of a mask shown without a cover operating in the second operational mode according to invention principles.

The change in configuration from the first operational mode to the second operational mode is shown in FIG. 16. FIG. 16 includes similar components in similar orientations as discussed above. In FIG. 16, the second pneumatic signal has been received from the second operational switch in the LDV and provided, via the signal gap in the LDV mask connector, to the signal input port 1218 of the mask 1200. The second pneumatic signal is communicated along the signal channel 1224 and received by the pneumatic actuator 1216. Upon receipt of the second pneumatic signal, a force is exerted on a piston within the pneumatic actuator 1216 causing the arm 1217 to extend outward from the pneumatic actuator 1216 in a direction indicated by the arrow labeled with reference numeral 1230. This extension of arm 1217 causes the connection arm 1219 to also move the direction of the arrow labeled 1230. The connection arm 1219 causes the bridge assembly to pivot about its respective pivot points described in FIG. 14 thereby rotating the bridge assembly 1212 and forcing the tab 1214 to compress the spring 1213 against the exhalation valve thereby placing the mask in the second operational mode.

Figure 17:
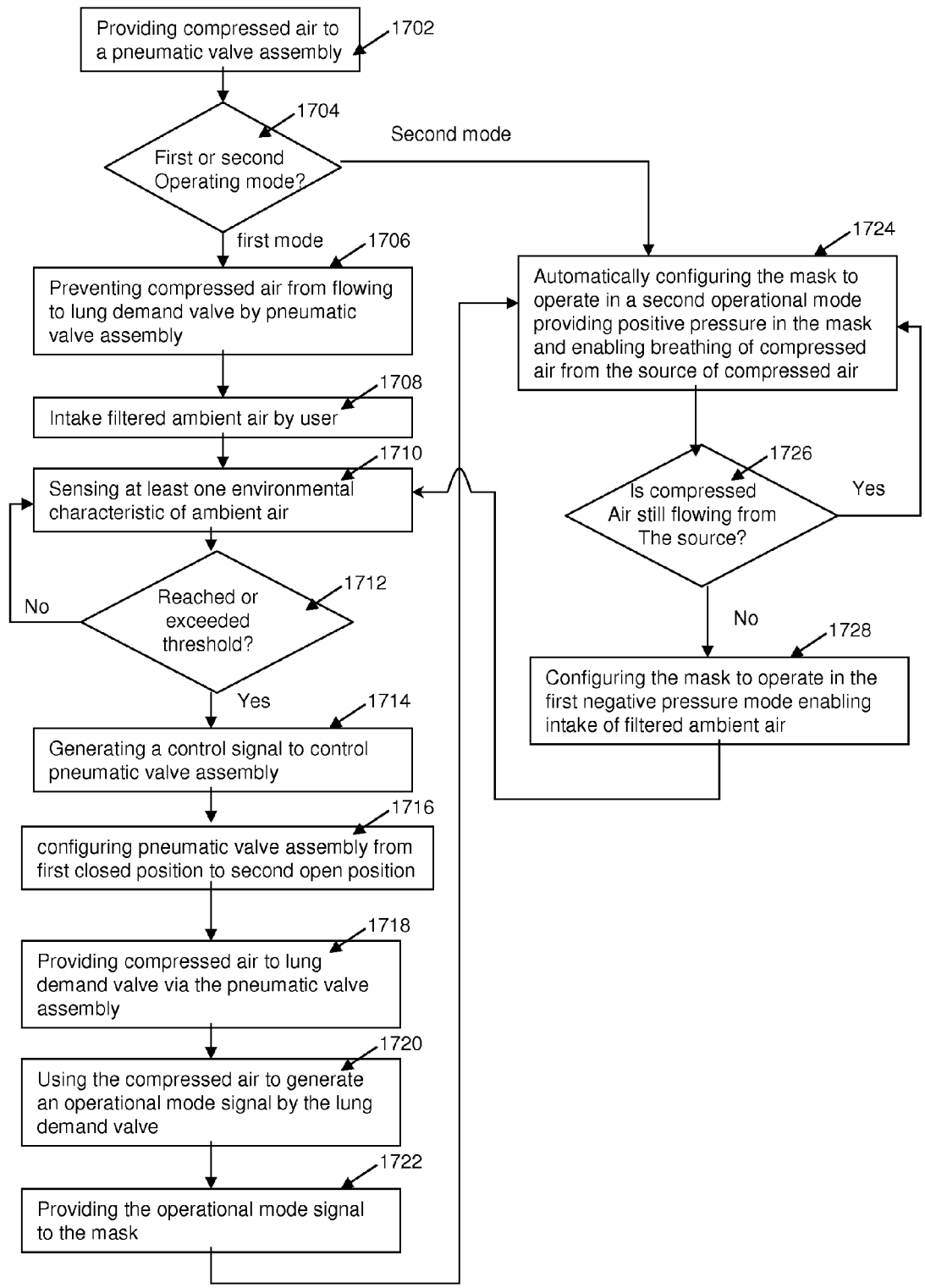
FIG. 17 is a flow diagram detailing operation of the breathing apparatus according to invention principles.

FIG. 17 is a flow diagram detailing the operation and use of the breathing apparatus described above with respects to FIGS. 1-16. In step 1702, compressed air is provided to a pneumatic valve assembly. In step 1704, a determination is made querying whether the apparatus is operating in the first operational mode or a second operational mode. If it is determined that the apparatus is operating in a first operational mode, then the compressed air is prevented from flowing to the lung demand valve and mask by a pilot valve assembly in step 1706. In step 1708, the user is able to intake filtered ambient air via a respirator or a power air purifying respirator. In step 1710, a sensor senses at least one environmental characteristic associated with the ambient air and a determination is made by a control processor in step 1712 as to whether or not the sensed at least one environmental characteristic has at least one of exceeded a threshold level or fallen below a threshold level indicating an alarm condition. If the result of the determination in step 1712 is negative, the method reverts back to step 1710. If the determination in step 1712 is positive, a control signal is generated in step 1714 and provided for controlling the pilot valve assembly to move from a first closed position to a second open position in step 1716. In step 1718, compressed air is provided to the lung demand valve via the pilot valve. In step 1720, a mode operational switch in the lung demand valve uses the compressed air to generate an operational mode signal. In step 1722, the operational mode signal is provided to the mask and the mask is automatically configured to operate in a second operational mode providing a positive pressure in the mask in step 1724. In step 1726, a determination is made as to whether or not compressed air is still flowing from the source. If the determination is positive, then the method reverts back to step 1724. IF the determination in step 1726 is negative, the mask is automatically configured to operate in a first operational mode and a negative pressure is provided in the mask. The method reverts back to step 1710 allowing the breathing apparatus to automatically determine when to switch from the first operational mode to the second operation mode.

Figure 18:
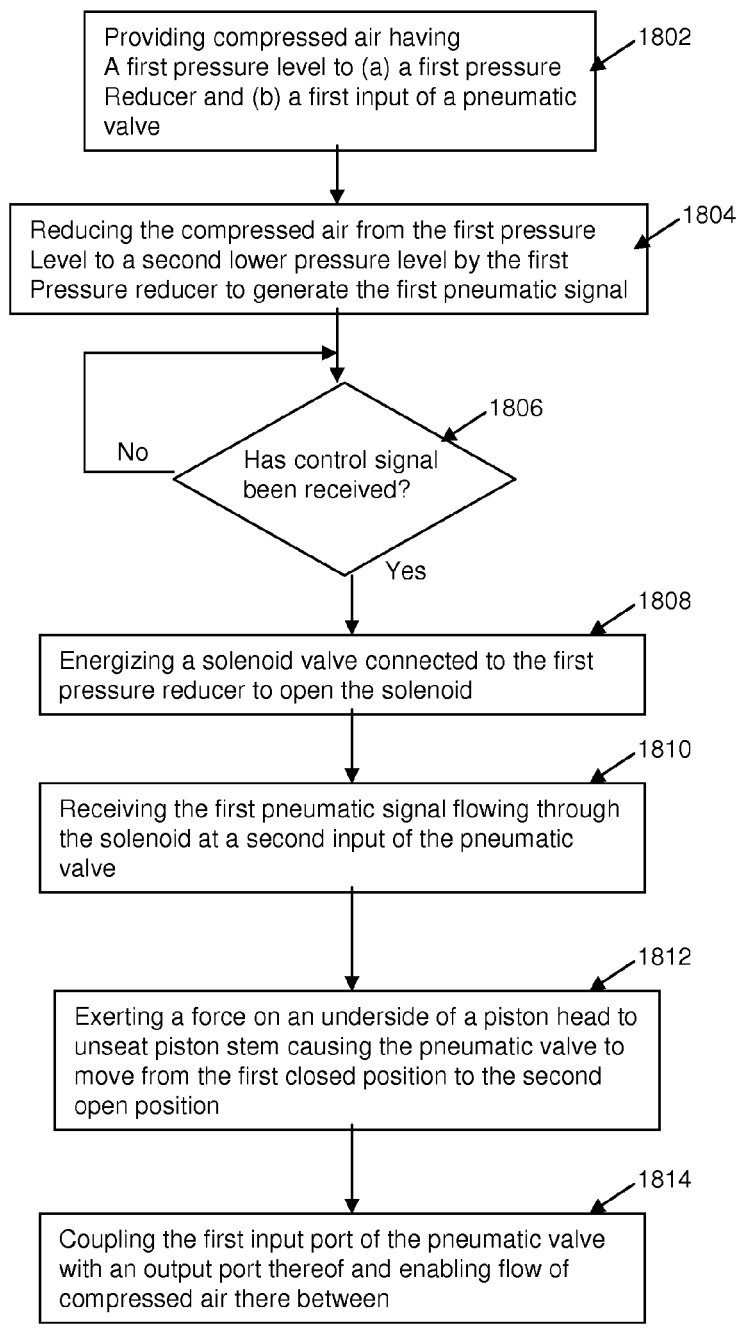
FIG. 18 is a flow diagram detailing operation of a pneumatic valve assembly of the breathing apparatus according to invention principles.

FIG. 18 is a flow diagram detailing the activities associated with configuring the pilot valve in step 1716 in FIG. 17. Compressed air having a first pressure level provided to (a) first pressure reducer and (b) an first input port of a pilot valve that is in a first closed position in step 1802. The first pressure reducer reduces the compressed air from the first pressure level to a second, lower pressure level to generate a first pneumatic signal in step 1804. A determination is made in step 1806 as to whether or not a control signal indicating that an alarm condition is present is received. If the determination is negative, the method reverts back to step 1806. If the determination in step 1806 is positive, a solenoid valve connected to the first pressure reducer is energized and opened in step 1808. The first pneumatic signal flows through the solenoid valve and is received at a second input of a pilot valve in step 1810. The first pneumatic signal exerts a force over a surface area on an underside of a piston head to unseat a stem of the piston causing the pilot valve to move from the first closed position to the second open position in step 1812. Compressed air at the first pressure level provided to the first input port of the pilot valve in step 1802 flows through an output port of the pilot valve in step 1814 and is further provided to a lung demand valve in step 1816.

Figure 19:
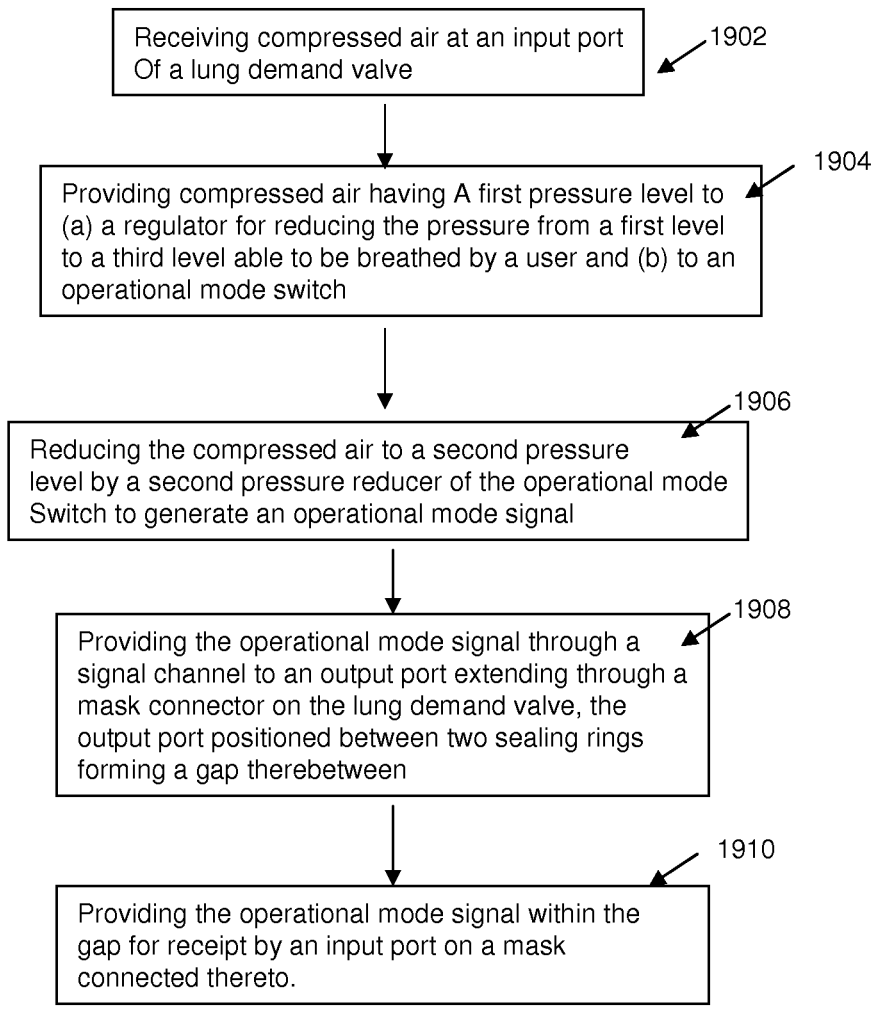
FIG. 19 is a flow diagram detailing operation of a lung demand valve of the breathing apparatus according to invention principles.

FIG. 19 is a flow diagram detailing the activities associated with generating the operational control signal shown in step 1720 of FIG. 17. In step 1902, compressed air having the first pressure level is received at an input port of the lung demand valve. The compressed air is provided to (a) a regulator for reducing the pressure from a first level to a third level able to be breathed by a user and (b) to an operational mode switch in step 1904. In step 1906 a second pressure reducer of the operational mode switch automatically reduces the pressure level of the compressed air from the first pressure level to a second lower pressure level to generate a second pneumatic signal representing the operational mode signal. In step 1908, the operational mode signal is provided through a signal channel to a signal output port extending through a mask connector on the lung demand valve. The signal output port is positioned between two sealing rings on the mask connector such that, upon connection of the lung demand valve to the mask, a sealed signal gap is formed by the two sealing devices and an inner wall of a lung demand valve connection port. The operational mode signal comprising the second pneumatic signal flows throughout the signal gap in step 1910 and is provided to a signal input port on a mask for controlling the mask to switch from the first operational mode where the mask has a negative pressure to the second operational mode where the mask has a positive pressure.

Figure 20:
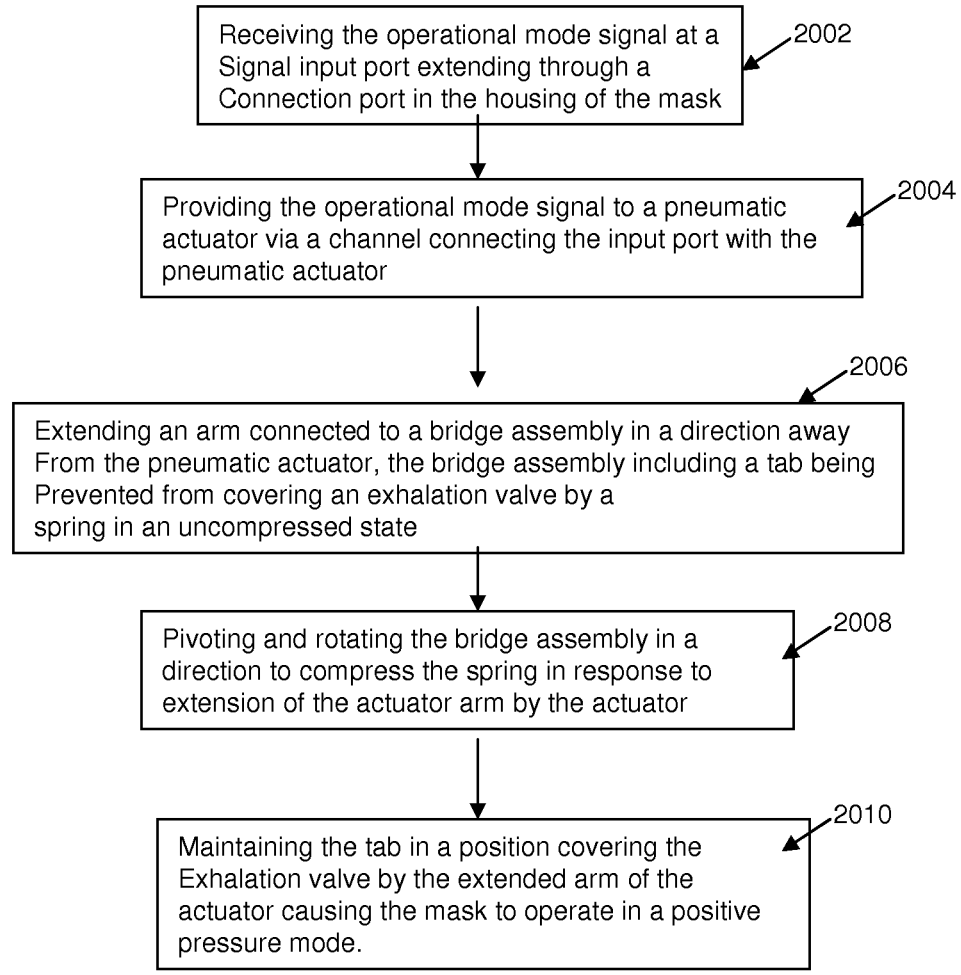
FIG. 20 is a flow diagram detailing operation of a mask of the breathing apparatus according to invention principles.

FIG. 20 is a flow diagram detailing the activities associated with automatically configuring the mask to operate in the second operational mode as stated in step 1724 in FIG. 17. At step 2002, the operational mode signal comprising the second pneumatic signal is received at a signal input port extending through a lung demand connection port in the housing of the mask. The operational mode signal is provided, in step 2004, to a pneumatic actuator via a signal channel connecting the signal input port to the pneumatic actuator. The pneumatic actuator extends an arm connected to a bridge assembly in a direction away from the pneumatic actuator in step 2006. The bridge assembly includes a tab for compressing a spring against an exhalation valve. In step 2008, the bridge assembly is caused to pivot and rotate in a direction to compress the spring against exhalation valve. In step 2010, the pneumatic actuator maintains the arm in an extended position thereby maintaining the spring pressure over the exhalation valve causing the mask to operate in the second operational mode and have a positive pressure therein.

The breathing apparatus described above in FIGS. 1-20 advantageously and automatically switches operational modes in response to sensing that at least one environmental characteristic has entered an alarm condition. The alarm condition may indicate that the ambient air in the environment has been contaminated with particulate matter or is saturated with gases other than oxygen. This contamination results in the breathing apparatus being unable to filter the ambient air and still provide a user with a sufficient level of breathable air via a wearable facemask. To compensate for the lack of breathable air, the breathing apparatus automatically provides air from a dedicated and clean source of compressed air to the facemask being worn by the user. By switching from filtered ambient air to the dedicated source of compressed air, a pressure state within the facemask is automatically switched from a negative pressure state to a positive pressure state thereby increasing the resistance of the compressed air from leaking through an exhalation valve in the mask. The breathing apparatus advantageously provides a pilot valve assembly that generates a first pneumatic signal and provides the first pneumatic signal to disengage a piston of a pilot valve in response to detecting an alarm condition associated with at least one environmental characteristic. Compressed air is able to flow through the pilot valve assembly into a lung demand valve which uses the compressed air to generate a second pneumatic signal for use in configuring the facemask to move from the first operational mode to the second operational mode. The second pneumatic signal is provided to the mask which automatically rotates a bridge assembly to further compress the exhalation valve spring against the exhalation valve and create a positive pressure state within the mask thereby causing the mask to operate in the second operational mode.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

I claim:

1. A breathing apparatus comprising:
 a source of compressed air;
 a lung demand valve that receives compressed air from said source;
 a pneumatic valve assembly connected between the source and the lung demand valve, said pneumatic valve assembly being moveable between a first closed position that prevents a flow of compressed air to the lung demand valve and a second open position that provides a path for compressed air to flow to the lung demand valve;

a mask that receives the lung demand valve therein, said mask providing the compressed air to a user, the mask having a first operational mode providing filtered ambient air to the user and a second operational mode providing compressed air to the user; and a control device coupled to the pneumatic valve assembly, said control device detecting a condition in air surrounding the apparatus and controlling the pneumatic valve assembly to move between the first closed and second open position and the mask to operate in a respective one of said first and second operational modes, wherein said lung demand valve includes:
  a housing;
  a connector extending from a surface of the housing enabling connection with the mask, the connector includes a first notch and a second notch extending around a perimeter of an exterior surface of the connector and separated by a gap; and
  an output port extending through the connector and positioned within the gap.

2. The breathing apparatus as recited in claim 1, wherein the compressed air is provided continuously from the source to the pneumatic valve assembly.

3. The breathing apparatus as recited in claim 1, wherein said control device includes a sensor and a control processor coupled to the sensor, the sensor sensing at least one environmental characteristic associated with ambient air and providing data representing said sensed at least one environment characteristic to the control processor.

4. The breathing apparatus as recited in claim 3, wherein said control processor compares the sensed data representing at least one environmental characteristic to a threshold value and determines if said sensed at least one environment characteristic represents an alarm condition, said control processor generates a control signal upon determining an alarm condition is present.

5. The breathing apparatus as recited in claim 3, wherein said sensor senses at least one of (a) oxygen; (b) carbon dioxide; (c) carbon monoxide; (d) hydrogen sulfide; (e) nitrogen dioxide; (f) sulfur dioxide; (g) phosphine; (h) hydrogen cyanide; (i) ammonia; G) Chlorine; (k) Hydrogen; (l) ozone; (m) nitrous oxide; (n) amines; (o) mercaptans; (p) phosgene; (q) any combustible atmospheric gaseous; (r) any combustible particulate matter; and (s) a presence of a contaminate.

6. The breathing apparatus as recited in claim 3, wherein said control device further comprises an adapter releaseably connected to said sensor and coupling said sensor to said control processor.

7. The breathing apparatus as recited in claim 6, wherein the sensor includes a wireless transmitter and the adapter includes a wireless receiver.

8. The breathing apparatus as recited in claim 1, wherein the pneumatic valve assembly includes an inlet coupled to said source for receiving compressed air;
  a first pressure reducer coupled to receive compressed air from the inlet, the first pressure reducer reducing a pressure of the compressed air to generate a first pneumatic signal;
  a pneumatic valve including
    a first input;
    a second input coupled to said inlet to receive compressed air having:
      an outlet coupled to said lung demand valve; and
      a piston moveable between a first position preventing the compressed air from flowing from the inlet to the outlet and a second position enabling the compressed air to flow from the inlet to the outlet; and
  a solenoid valve coupled between the first pressure reducer and the first input of the pneumatic valve, the solenoid moveable between a first closed position preventing passage of the first pneumatic signal from the first pressure reducer to the pneumatic valve and a second open position enabling passage of the first pneumatic signal from the first pressure reducer to the pneumatic valve, wherein compressed air is prevented from flowing from said second input to the outlet of the pneumatic valve assembly when said solenoid is in the first closed position and compressed air is permitted to flow from said second input to the outlet of the pneumatic valve assembly when the solenoid is in the second open position.

9. The breathing apparatus as recited in claim 8, wherein said control device controls said solenoid to move between the first closed position to the second open position by generating a control signal upon detecting the condition in the air surrounding the apparatus.

10. The apparatus as recited in claim 9, wherein upon moving said solenoid into said second open position, said first pneumatic signal is provided to the first input port causing the piston to move from the first closed position to the second open position connecting said second input port with said outlet of said pneumatic valve assembly.

11. The breathing apparatus as recited in claim 1, wherein said lung demand valve further includes an operational mode switch connected to provide a second pneumatic signal to said output port extending through said connector.

12. The breathing apparatus as recited in claim 11, wherein said operational mode switch includes a second pressure reducer that receives compressed air having a first pressure level and generating the second pneumatic signal by reducing the compressed air to a second pressure level.

13. The breathing apparatus as recited in claim 1, wherein the first notch includes a first sealing device and a second notch includes a second sealing device, the first and second sealing devices sealing isolating the gap to maintain the second pneumatic signal within the gap.

14. The breathing apparatus as recited in claim 11, wherein the mask includes a faceplate and a connection section enabling connection of the mask to the lung demand valve, the connection section including
  an exhalation valve that enables air to flow out from within the mask;
  a bridge assembly;
  a spring connecting the bridge assembly to the exhalation valve, the spring moveable between an uncompressed position allowing air to selectively flow through the exhalation valve and a compressed position increasing a resistance on the air from flowing through the exhalation valve and reducing an amount of air able to flow out therefrom; and
  an actuator connected to the bridge assembly, wherein in response to the second pneumatic control signal, the actuator and the bridge assembly cause the spring to move between the uncompressed and compressed positions.

15. The breathing apparatus as recited in claim 14, wherein the connection section further includes a port for receiving the connector of the lung demand valve, the port having an aperture extending therethrough and aligned with the gap to receive the second pneumatic signal therethrough.

16. The breathing apparatus as recited in claim 15, wherein said connection section further comprises a channel connecting the aperture to the actuator to provide the second pneumatic signal to the actuator, the actuator causing the bridge assembly to compress the spring over the exhalation valve upon receipt of the second pneumatic signal.

17. The breathing apparatus as recited in claim 1, further comprising an indicator coupled to the mask, the indicator indicating information associated with at least one of the detected condition and a mode of operation, wherein said control device communicates data representing the information to the indicator for selectively controlling the indicator to indicate the information.

18. The breathing apparatus as recited in claim 17, wherein said indicator is a visual indicator and is able to uniquely indicate at least one of (a) respective different types of conditions detected by the control device and (b) operational modes of the apparatus.

19. The breathing apparatus as recited in claim 14, wherein said mask is operable in a first negative pressure mode when said spring is in said uncompressed position and a second positive pressure mode when said spring is in said compressed position.

20. A breathing apparatus comprising:
a lung demand valve comprising:
a housing;
a connector extending from a surface of the housing, the connector includes a first notch and a second notch extending around a perimeter of an exterior surface of the connector and separated by a gap; and
an output port extending through the connector and positioned within the gap.

21. The breathing apparatus of claim 20 further comprising:
an operational mode switch connected to provide a pneumatic signal to an output port extending through the connector.

* * * * *